United States Patent
Large

(10) Patent No.: US 9,669,030 B2
(45) Date of Patent: Jun. 6, 2017

(54) HYDANTOIN DERIVATIVES AS KV3 INHIBITORS

(71) Applicant: AUTIFONY THERAPEUTICS LIMITED, London (GB)

(72) Inventor: Charles Large, Verona (IT)

(73) Assignee: AUTIFONY THERAPEUTICS LIMITED, London (GB)

( * ) Notice: Subject to any disclaimer, the term of this patent is extended or adjusted under 35 U.S.C. 154(b) by 30 days.

(21) Appl. No.: 14/403,011

(22) PCT Filed: May 22, 2013

(86) PCT No.: PCT/GB2013/051343
§ 371 (c)(1),
(2) Date: Nov. 21, 2014

(87) PCT Pub. No.: WO2013/175211
PCT Pub. Date: Nov. 28, 2013

(65) Prior Publication Data
US 2015/0157631 A1 Jun. 11, 2015

(30) Foreign Application Priority Data

May 22, 2012 (GB) .................... 1209013.0
Jun. 6, 2012 (GB) .................... 1209986.7
Dec. 13, 2012 (GB) .................... 1222528.0

(51) Int. Cl.
| | |
|---|---|
| *A61K 31/506* | (2006.01) |
| *C07D 405/14* | (2006.01) |
| *C07D 307/94* | (2006.01) |
| *C07D 311/76* | (2006.01) |
| *C07D 401/04* | (2006.01) |
| *C07D 403/04* | (2006.01) |
| *C07D 405/12* | (2006.01) |
| *C07D 307/87* | (2006.01) |
| *A61K 31/4439* | (2006.01) |

(52) U.S. Cl.
CPC ........ *A61K 31/506* (2013.01); *A61K 31/4439* (2013.01); *C07D 307/87* (2013.01); *C07D 307/94* (2013.01); *C07D 311/76* (2013.01); *C07D 401/04* (2013.01); *C07D 403/04* (2013.01); *C07D 405/12* (2013.01); *C07D 405/14* (2013.01)

(58) Field of Classification Search
CPC .. C07D 307/87; C07D 307/94; C07D 311/76; C07D 401/04; C07D 403/04; C07D 405/12; C07D 405/14; A61K 31/506; A61K 31/4439
See application file for complete search history.

(56) References Cited

U.S. PATENT DOCUMENTS

| | | |
|---|---|---|
| 4,350,701 A | 9/1982 | Rentzea et al. |
| 4,675,403 A | 6/1987 | Abou-Gharbia et al. |
| 4,804,671 A | 2/1989 | Costin et al. |
| 5,362,878 A | 11/1994 | Chang et al. |
| 5,637,729 A | 6/1997 | Lacroix et al. |

(Continued)

FOREIGN PATENT DOCUMENTS

| | | | |
|---|---|---|---|
| DE | 38 36 175 A1 | 5/1990 | |
| EP | 0 277 842 A1 | 8/1988 | |
| EP | 0 368 008 A1 | 5/1990 | |
| EP | 0 726 898 B1 | 12/2000 | |
| EP | 1 206 935 A1 | 5/2002 | |
| FR | WO 2012076777 A1 * | 6/2012 | ............ F02N 11/08 |
| GB | 2 216 890 A | 10/1989 | |
| IT | WO 2011069951 A1 * | 6/2011 | ........... C07D 233/76 |
| JP | 11279129 A | 10/1999 | |
| JP | 2000072731 A | 3/2000 | |
| JP | 2000336071 A | 12/2000 | |
| WO | WO 91/04027 | 4/1991 | |

(Continued)

OTHER PUBLICATIONS

U-R Heinrich et al., 3 Drug Discovery Today: Disease Mechanisms, 131-136 (2006).*

(Continued)

*Primary Examiner* — Alexander R Pagano
(74) *Attorney, Agent, or Firm* — Nixon & Vanderhye P.C.

(57) ABSTRACT

The present invention relates to the prophylaxis of acute noise-induced hearing loss by administering a compound of formula (I): wherein: W is group (Wa), group (Wb) or group (Wc):

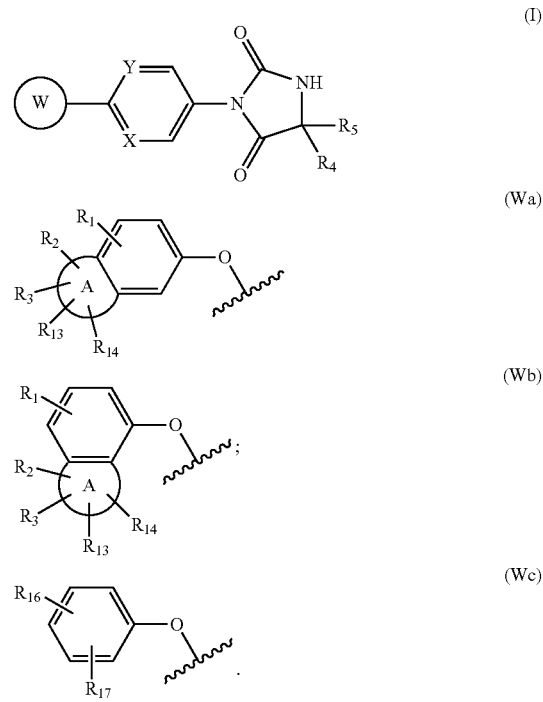

20 Claims, No Drawings

(56) References Cited

U.S. PATENT DOCUMENTS

| | | | |
|---|---|---|---|
| 5,656,634 | A | 8/1997 | Chang et al. |
| 5,703,087 | A | 12/1997 | Perregaard et al. |
| 8,722,695 | B2* | 5/2014 | Alvaro ................. C07D 233/76 514/274 |
| 9,133,175 | B2* | 9/2015 | Alvaro ................. C07D 405/12 |
| 2003/0008884 | A1 | 1/2003 | Gerusz et al. |
| 2003/0149061 | A1 | 8/2003 | Nishihara et al. |
| 2005/0009817 | A1 | 1/2005 | Savoy et al. |
| 2005/0153968 | A1 | 7/2005 | Bi et al. |
| 2007/0004753 | A1 | 1/2007 | Sawyers et al. |
| 2007/0254933 | A1 | 11/2007 | Jung et al. |
| 2008/0139634 | A2 | 6/2008 | Jung et al. |
| 2008/0261961 | A1 | 10/2008 | Flynn et al. |
| 2010/0158860 | A1 | 6/2010 | Steiner et al. |
| 2010/0172975 | A1 | 7/2010 | Sawyers et al. |
| 2010/0210665 | A1 | 8/2010 | Sawyers et al. |
| 2011/0003839 | A1 | 1/2011 | Jung et al. |
| 2011/0112097 | A1 | 5/2011 | Jaehne et al. |
| 2011/0123490 | A1 | 5/2011 | Schoenfeld et al. |
| 2012/0190718 | A1 | 7/2012 | Jung et al. |
| 2012/0289526 | A1 | 11/2012 | Alvaro et al. |
| 2013/0267510 | A1* | 10/2013 | Alvaro ................. C07D 405/12 514/230.5 |
| 2014/0107139 | A1* | 4/2014 | Alvaro ................. C07D 307/87 514/274 |
| 2015/0111910 | A1* | 4/2015 | Marasco .............. C07D 405/14 514/274 |

FOREIGN PATENT DOCUMENTS

| | | |
|---|---|---|
| WO | WO 96/36229 | 11/1996 |
| WO | WO 96/36633 | 11/1996 |
| WO | WO 97/00612 | 1/1997 |
| WO | WO 98/05652 | 2/1998 |
| WO | WO 98/23155 | 6/1998 |
| WO | WO 98/23156 | 6/1998 |
| WO | WO 98/33382 | 8/1998 |
| WO | WO 01/76582 A1 | 10/2001 |
| WO | WO 03/048134 A1 | 6/2003 |
| WO | WO 03/066050 A1 | 8/2003 |
| WO | WO 2004/099159 A1 | 11/2004 |
| WO | WO 2005/000309 A2 | 1/2005 |
| WO | WO 2005/049040 A1 | 6/2005 |
| WO | WO 2005/049580 A1 | 6/2005 |
| WO | WO 2006/071471 A2 | 7/2006 |
| WO | WO 2006/124118 A1 | 11/2006 |
| WO | WO 2007/126765 A2 | 11/2007 |
| WO | WO 2007/127010 A2 | 11/2007 |
| WO | WO 2010/072598 A1 | 7/2010 |
| WO | WO 2011/069951 | 6/2011 |
| WO | WO 2011/073114 A1 | 6/2011 |
| WO | WO 2011069951 A1 * | 6/2011 |
| WO | WO 2012/076877 | 6/2012 |
| WO | WO 2012/168710 | 12/2012 |
| WO | WO 2012/168710 A1 | 12/2012 |
| WO | WO 2013/083994 A1 | 6/2013 |
| WO | WO 2013/175211 A1 | 11/2013 |
| WO | WO 2013/175215 A1 | 11/2013 |
| WO | WO 2013/182850 A1 | 12/2013 |
| WO | WO 2013/182851 A1 | 12/2013 |

OTHER PUBLICATIONS

A.S. Nordmann et al., 139 Hearing Research, 13-30 (2000).*
W. Li et al., 437 The Journal of Comparative Neurology, 196-218 (2001).*
C.A. von Hehn et al., 24 The Journal of Neuroscience, 1936-1940 (2004).*
D.K. Jung et al., 27 Neurological Research, 436-440 (2005).*
N. Pilati et al., 283 Hearing Research, 98-106 (2012).*
Harte et al, "Efficacy and relevance of the modulation of Kv3 channels to alleviate cognitive dysfunction in an animal model of schizophrenia symptomatology", Abstract 4th Biennial Schizophrenia International Research Conference Apr. 2014 (1 page).
Leger et al, "Two novel KV3 ion channel modulators alleviate cognitive dysfunction and social behaviour deficits of relevance to schizophrenia in an animal model", Abstract 4th Biennial Schizophrenia International Research Conference Apr. 2014 (1 page).
Mabrouk et al, "A novel Kv3 positive modulator augments gamma frequency oscillations in the mammalian neocortex in vitro", Abstract 4th Biennial Schizophrenia International Research Conference Apr. 2014 (1 page).
Neill et al, "A novel Kv3 ion channel modulator restores cognitive function in an animal model of cognitive impairment in schizophrenia", Abstract European College of Neuropsychopharmacology conference Oct. 2013 (2 page).
Sidor et al, Abstract Society for Neuroscience Annual Meeting Oct. 2012 (1 page).
Aroniadou-Anderjaska et al, "Mechanisms regulating GABAergic inhibitory transmission in the basolateral amygdala: implications for epilepsy and anxiety disorders", Amino Acids (2007) 32:305-315.
Atzori et al, "$H_2$ histamine receptor-phosphorylation of Kv3.2 modulates interneuron fast spiking", Nature Neuroscience, vol. 3, No. 8, Aug. 2000, 791-798.
Ben-Ari, "Seizures Beget Seizures: The Quest for GABA as a Key Player", Critical Reviews™ in Neurobiology 18(1-2):135-144, 2006.
Benes et al, "Circuitry-based gene expression profiles in GABA cells of the trisynaptic pathway in schizophrenics versus bipolars", PNAS, Dec. 30, 2008, vol. 105, No. 52, pp. 20935-20940.
Berge et al, "Pharmaceutical Salts", Journal of Pharmaceutical Sciences, vol. 66, No. 1, Jan. 1977, pp. 1-19.
Brambilla et al, "GABAergic dysfunction in mood disorders", Molecular Psychiatry (2003) 8, 721-737.
Bramness et al, "Amphetamine-induced psychosis—a separate diagnostic entity or primary psychosis triggered in the vulnerable?", BMC Psychiatry, 12, pp. 1-7, 2012.
Campbell et al, "D-methionine (D-met) significantly rescues noise-induced hearing loss: Timing studies", Hearing Research 282 (2011) 138-144.
Chang et al, "Distribution of Kv3.3 Potassium Channel Subunits in Distinct Neuronal Populations of Mouse Brain", The Journal of Comparative Neurology, 502:953-972 (2007).
Chow et al, "K[+] Channel Expression Distinguishes Subpopulations of Parvalbumin-and Somatostatin-Containing Neocortical Interneurons", The Journal of Neuroscience, Nov. 1, 1999 19(21):9332-9345.
Costall et al, "A Primate Model for the Assessment of Anxiolytic Drug Action", Brit. J. Pharmacol., 95, pp. 475P, 1988.
Desai et al, "Protein Kinase C Modulates Inactivation of Kv3.3 Channels", The Journal of Biological Chemistry, vol. 283, No. 32, pp. 22283-22294, Aug. 8, 2008.
Diochot et al, "Sea Anemone Peptides with a Specific Blocking Activity against the Fast Inactivating Potassium Channel Kv3.4", The Journal of Biological Chemistry, vol. 273, No. 12, pp. 6744-6749, 1998.
Engel et al, Dynamic Predictions: Oscillations and Synchrony in Top-Down Processing, Nature Reviews Neuroscience, vol. 2, pp. 704-716, Oct. 2001.
Espinosa et al, "Alcohol Hypersensitivity, Increased Locomotion, and Spontaneous Myoclonus in Mice Lacking the Potassium Channels Kv3.1 and Kv3.3", The Journal of Neuroscience, 21(17):6657-6665, Sep. 1, 2001.
Espinosa et al, "Ablation of Kv3.1 and Kv3.3 Potassium Channels Disrupts Thalamocortical Oscillations In Vitro and In Vivo", The Journal of Neuroscience, 28(21):5570-5581, May 21, 2008.
Fisahn, "Kainate receptors and rhythmic activity in neuronal networks: hippocampal gamma oscillations as a tool", J. Physiol, 562.1, pp. 65-72, 2005.
Goldman et al, "Hearing loss and tinnitus—the hidden healthcare time bomb", Drug Discovery Today, vol. 15, Nos. 7/8, pp. 253-255, Apr. 2010.

(56) References Cited

OTHER PUBLICATIONS

Hawkins et al, "Sketches of Otohistory Part 10: Noise-Induced Hearing Loss", Audiol. Neurotol., 10, pp. 305-309, 2005.
Henderson et al, "The Role of Oxidative Stress in Noise-Induced Hearing Loss", Ear & Hearing, 27, pp. 1-19, 2006.
Humes et al, "Noise and Military Service: Implications for Hearing Loss and Tinnitus", (2006); 339 pages.
Jastreboff et al, "Neurophysiological model of tinnitus: Dependence of the minimal masking level on treatment outcome", Hearing Research, 80, pp. 216-232, 1994.
Joho et al, "Increased γ- and Decreased δ-Oscillations in a Mouse Deficient for a Potassium Channel Expressed in Fast-Spiking Interneurons", J. Neurophysiol., 82, pp. 1855-1864, 1999.
Jones et al, "Animal Models of Schizophrenia", Brit. J. Pharmacol., 164, pp. 1162-1194, 2011.
Jung et al, "Age-related changes in the distribution of Kv1.1 and Kv3.1 in rat cochlear nuclei", Neurol. Res., 27, pp. 436-440, 2005.
Kaczmarek et al, "Regulation of the timing of MNTB neurons by short-term and long-term modulation of potassium channels", Hearing Res., 206, pp. 133-145, 2005.
Kasten et al, "Differential regulation of action potential firing in adult murine thalamocortical neurons by Kv3.2, Kv1 and SK potassium and N-type calcium channels", J. Physiol., 584.2, pp. 565-582, 2007.
Kujawa et al, "Acceleration of Age-Related Hearing Loss by Early Noise Exposure: Evidence of a Misspent Youth", J. Neurosci., 26(7), pp. 2115-2123, 2006.
Lau et al, "Impaired Fast-Spiking, Suppressed Cortical Inhibition, and Increased Susceptibility to Seizures in Mice Lacking Kv3.2 $K^+$ Channel Proteins", J. Neurosci., 20(24), pp. 9071-9085, 2000.
Lewis et al, "Cortical parvalbumin interneurons and cognitive dysfunction in schizophrenia", Trends in Neurosciences, 35(1), pp. 57-67, 2012.
Li et al, "Localization of Two High-Threshold Potassium Channel Subunits in the Rat Central Auditory System", J. Comp. Neurol., 437, pp. 196-218, 2001.
Lisman, "Excitation, inhibition, local oscillations, or large-scale loops: what causes the symptoms of schizophrenia?", Curr. Opin. Neurobiol., 22(3), pp. 537-544, 2012.
Markram et al, "Interneurons of the Neocortical Inhibitory System", Nat. Rev. Neurosci., 5, pp. 793-807, 2004.
Martina et al, "Functional and Molecular Differences between Voltage-Gated $K^+$ Channels of Fast-spiking Interneurons and Pyramidal Neurons of Rat Hippocampus", J. Neurosci., 18(20), pp. 8111-8125, 1998.
Mazelova et al, "Auditory function in presbycusis: preipheral vs. central changes", Experimental Gerontology, 38, pp. 87-94, 2003.
McDonald et al, "Differential Expression of Kv3.1b and Kv3.2 Potassium Channel Subunits in Interneurons of the Basolateral Amygdala", Neuroscience, 138, pp. 537-547, 2006.
McMahon et al, "Allele-dependent changes of olivocerebellar circuit properties in the absence of the voltage-gated potassium channels Kv3.1 and Kv3.3", Eur. J. Neurosci., 19, pp. 3317-3327, 2004.
Meikle et al, "The Tinnitus Functional Index: Development of a New Clinical Measure for Chronic, Intrusive Tinnitus", Ear & Hearing, 33(2), pp. 153-176, 2012.
Minassian et al, "Altered Kv3.3 channel gating in early-onset spinocerebellar ataxia type 13", J. Physiol., 590.7, pp. 1599-1614, 2012.
Newman et al, "Development of the Tinnitus Handicap Inventory", Arch. Otolaryngol Head Neck Surg., 122, pp. 143-148, 1996.
Nilsson et al, "Development of the Hearing in Noise Test for the measurement of speech reception thresholds in quiet and in noise", J. Acoust. Soc. Am., 95(2), pp. 1085-1099, 1994.
Oishi et al, "Emerging treatments for noise-induced hearing loss", Exp. Opin. Emerg. Drugs, 16(2), pp. 235-245, 2011.
Pilati et al, "Acoustic over-exposure triggers burst firing in dorsal cochlear nucleus fusiform cells", Hearing Research, 283, pp. 98-106, 2012.
Puente et al, "Precise localization of the voltage-gated potassium channel subunits Kv3.1b and Kv3.3 revealed in the molecular layer of the rat cerebellar cortex by a pre-embedding immunogold method", Histochem. Cell Biol., 134, pp. 403-409, 2010.
Reynolds et al, "Calcium Binding Protein Markers of GABA Deficits in Schizophrenia—Post Mortem Studies and Animal Models", Neurotox. Res., 6, pp. 57-62, 2004.
Roberts et al, " Ringing Ears: The Neuroscience of Tinnitus", J. Neurosci., 30(45), pp. 14972-14979, 2010.
Rudy et al, "Kv3 channels: voltage-gated $K^+$ channels designed for high-frequency repetitive firing", Trends in Neurosciences, 24(9), pp. 517-526, 2001.
Sacco et al, "Properties and expression of Kv3 channels in cerebellar Purkinje cells", Mol. Cell. Neurosci., 33, pp. 170-179, 2006.
Schulz et al, "Neurobiology of Circadian Systems", CNS Drugs, 23 Suppl 2, pp. 3-13, 2009.
Shield, "Evaluation of the social and economic costs of hearing impairment", A report for Hear-It AISBL: www.hear-it.org/multimedia/Hear_It_Report_October_2006.pdf, 2006.
Slepecky, "Overview of mechanical damage to the inner ear: noise as a tool to probe cochlear function", Hearing Research, 22, pp. 307-321, 1986.
Song et al, "Acoustic environment determines phosphorylation state of the Kv3.1 potassium channel in auditory neurons", Nat. Neurosci., 8(10), pp. 1335-1342, 2005.
Spencer et al, "Neural synchrony indexes disordered perception and cognition in schizophrenia", PNAS, 101(49), pp. 17288-17293, 2004.
Stean et al, "Postsynaptic $5-HT_{1B}$ receptors modulate electroshock-induced generalised seizures in rats", Brit. J. Pharmacol., 144, pp. 628-635, 2005.
Strumbos et al, "Specific and Rapid Effects of Acoustic Stimulation on the Tonotopic Distribution of Kv3.1b Potassium Channels in the Adult Rat", Neuroscience, 167, pp. 567-572, 2010.
Strumbos et al, "Fragile X Mental Retardation Protein Is Required for Rapid Experience-Dependent Regulation of Potassium Channel Kv3.1b", J. Neuroscience, 30(31), pp. 10263-10271, 2010.
Turner, "Behavioral measures of tinnitus in laboratory animals", Prog. Brain Res., 166, pp. 147-156, 2007.
Von Hehn et al, "Loss of Kv3.1 Tonotopicity and Alterations in cAMP Response Element-Binding Protein Signaling in Central Auditory Neurons of Hearing Impaired Mice", J. Neurosci., 24(8), pp. 1936-1940, 2004.
Waters et al, "Mutations in voltage-gated potassium channel KCNC3 cause degenerative and developmental central nervous system phenotypes", Nature Genetics, 38(4), pp. 447-451, 2006.
Weiser et al, "Differential Expression of Shaw-related $K^+$ Channels in the Rat Central Nervous System", J. Neurosci., 14(3), pp. 949-972, 1994.
Yamane et al, "Appearance of free radicals in the guinea pig inner ear after noise-induced acoustic trauma", Eur. Arch. Oto-Rhino-Laryngol., 252, pp. 504-508, 1995.
Yanagi et al, "Kv3.1-containing $K^+$ channels are reduced in untreated schizophrenia and normalized with antipsychotic drugs", Molecular Psychiatry, pp. 1-7, 2013.
Yeung et al, "Modulation of Kv3 Subfamily Potassium Currents by the Sea Anemone Toxin BDS: Significance for CNS and Biophysical Studies", J. Neurosci., 25(38), pp. 8735-8745, 2005.
Zhang et al, "Total synthesis and reassignment of stereochemistry of obyanamide", Tetrahedron, 62, pp. 9966-9972, 2006.
International Search Report and Written Opinion mailed Mar. 18, 2011, issued in connection with PCT/EP2010/068946.
International Search Report and Written Opinion mailed Feb. 24, 2012, issued in connection with PCT/GB2011/052414.
International Search Report and Written Opinion mailed Jul. 13, 2012, issued in connection with PCT/GB2012/051278.
International Search Report and Written Opinion mailed Jan. 25, 2013, issued in connection with PCT/GB2012/053045.
International Search Report and Written Opinion mailed Jul. 12, 2013, issued in connection with PCT/GB2013/051347.
International Preliminary Report on Patentability mailed Apr. 30, 2014, issued in connection with PCT/GB2013/051343.

(56) References Cited

OTHER PUBLICATIONS

International Search Report for PCT/GB2013/051343, mailed Jul. 8, 2013, Bosma, Peter.
Written Opinion of the International Searching Authority for PCT/GB2013/051343, mailed Jul. 8, 2013, Bosma, Peter.
Response to Written Opinion dated Mar. 18, 2014, for PCT/GB2013/051343, (Autifony Therapeutics Limited).

* cited by examiner

HYDANTOIN DERIVATIVES AS KV3 INHIBITORS

This application is the U.S. national phase of International Application No. PCT/GB2013/051343, filed 22 May 2013, which designated the U.S. and claims priority to GB Application No. 1209013.0, filed 22 May 2012; GB Application No. 1209986.7, filed 6 Jun. 2012; and GB Application No. 1222528.0, filed 13 Dec. 2012, the entire contents of each of which are hereby incorporated by reference.

TECHNICAL FIELD

This invention relates to compounds and pharmaceutical compositions containing such compounds for use in the prophylaxis of acute noise-induced hearing loss.

BACKGROUND TO THE INVENTION

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (Sacco et al., 2006, Mol. Cell. Neurosci. 33, 170-179; Puente et al., 2010, Histochem. Cell Biol. 134, 403-409), and auditory brain stem nuclei (Li et al., 2001, J. Comp. Neurol. 437, 196-218).

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www.hear-it.org/multimedia/Hear_It_Report_October_2006.pdf). In some cases, hearing loss can occur rapidly over a period of hours or days. Such acute hearing loss may be caused by exposure to loud noise, ear infection or other idiopathic causes. The most common of these, noise-induced hearing loss was estimated to have a prevalence of 1.35% of the population in Western countries in 2009; thus affecting, for example, over 4 million Americans (Noise Induced Hearing Loss Market Report, prepared by RNID, 2009). Treatment for acute hearing loss is currently limited to oral or intratympanic administration of steroidal anti-inflammatory agents, such as dexamethasone. The steroids are typically administered as soon as possible after the symptoms of hearing loss present, and treatment is continued thereafter.

A complete picture of the effect of excessive noise on the auditory system has yet to be determined. However, the effect of excessive noise on certain parts of the auditory system has been evaluated. For example, noise trauma can result in two types of injury to the inner ear, depending on the intensity and duration of the exposure: transient attenuation of hearing acuity, a so-called "temporary threshold shift" (TTS), or a permanent threshold shift (PTS). There is growing evidence that different physiological processes might underlie the two manifestations of noise exposure, although some overlap is likely (Oishi and Schacht Expert. Opin. Emerg. Drugs. 2011 June; 16(2): 235-245).

TTS is a temporary shift of the auditory threshold which causes a temporary loss of hearing. Hearing generally recovers within 24-48 hours (Humes et al. Noise and military service implications for hearing loss and tinnitus. Washington, D.C.: National Academies Press; 2005). PTS is more generally associated with long-term exposure to noise. However, depending on the intensity, frequency and duration of the noise event, permanent hearing loss (PTS) may occur after a single, isolated noise event. Furthermore, even if a noise event apparently results in a TTS (i.e. hearing appears to recover without intervention) a mouse model has indicated that TTS at young ages accelerated age-related hearing loss, even though hearing thresholds were completely restored shortly after the TTS (Kujawa et al. J. Neurosci. 2006; 26:2115-2123. [PubMed: 16481444]).

The changes in the inner ear which lead to the auditory threshold shift are not well understood, but it is thought that intense noise can cause mechanical damage (via vibration) and/or metabolic stress that triggers hair cell death (Slepecky. Hear. Res. 1986; 22:307-321 [PubMed: 3090001]; Hawkins et al. Audiol. Neurootol. 2005; 10: 305-309 [PubMed: 16103641]; Henderson et al. Ear Hear. 2006; 27:1-19 [PubMed: 16446561]). Current theories of metabolic damage centre on the formation of reactive oxygen species (free radicals, ROS) evoked by excessive noise stimulation, followed by activation of apoptotic signalling pathways to cell death. ROS emerge immediately after noise exposure and persist for 7-10 days thereafter, spreading apically from the basal end of the organ of the Corti, thus widening the area of damage (Yamane et al. Eur. Arch. Otorhinolaryngol. 1995; 252:504-508 [PubMed: 8719596]). As such, a window of opportunity potentially exists for post-exposure intervention to prevent hearing loss. Upon exposure to excessive noise, $Ca^{2+}$ levels have also been observed to increase and cochlear blood flow has been observed to decrease, therefore these parameters have also been implicated in hair cell damage (Oishi and Schacht Expert. Opin. Emerg. Drugs. 2011 June; 16(2): 235-245).

A variety of treatments for preventing hair cell death have been investigated in animal models. For example, antioxidants have been found to attenuate noise-induced hearing loss when applied prior to noise exposure, and treatments up to 3 days after exposure were also found to be effective to some degree (Oishi and Schacht Expert. Opin. Emerg. Drugs. 2011 June; 16(2): 235-245).

The physical damage to the inner ear caused by exposure to excessive noise results in reduced or altered activity in the auditory nerve, which can lead to changes in the central auditory system. These changes can result in a range of hearing loss symptoms in addition to the shift in hearing threshold. For example, tinnitus may follow as a result of adaptive changes in central auditory pathways from brainstem to auditory cortex (Roberts et al., 2010, J. Neurosci. 30, 14972-14979). Changes in the central auditory processing system could also result in the impairment of auditory temporal processing, thereby causing difficulties in speech perception. Central auditory mechanisms also feedback to the outer hair cells of the cochlea, via the medial olivocochlear pathway, and can up or down-regulate the sensitivity of the cochlea to sound. Damage to this feedback mechanism following noise trauma may affect how the cochlea responds to loud sounds, and could render the cochlea more vulnerable to future damage.

However, although the use of pharmaceutical protectants to prevent/reduce inner ear damage has shown some promise in animal models, the primary preventative strategy for avoiding noise-induced hearing loss in humans is still the use of physical ear protectors such as ear plugs. Shielding the ears from noise may be undesirable, particularly in industrial and military settings where sensory perception via hearing is critical. Thus, there is a need for an effective preventative approach to noise-induced hearing loss in the form of a pharmaceutical compound. Suitably, the compound can be administered safely by the oral route.

Kv3.1 and Kv3.3 channels are expressed at high levels in auditory brainstem nuclei (Li et al., 2001, J. Comp. Neurol. 437, 196-218), and by neurons of the auditory nerve, which transmits auditory information from the cochlea to the auditory brainstem. Phosphorylation of Kv3.1 and Kv3.3 channels in auditory brainstem neurons is suggested to contribute to the rapid physiological adaptation to sound levels that may play a protective role during exposure to noise (Desai et al., 2008, J. Biol. Chem. 283, 22283-22294; Song et al., Nat. Neurosci. 8, 1335-1342). Furthermore, a loss of Kv3 channel function has been shown to be associated with noise-trauma induced hearing loss (Pilati et al., 2012, Hear. Res. 283, 98-106), and may contribute to the adaptive changes that give rise to tinnitus in many patients following noise-induced hearing loss. As discussed above, tinnitus may follow noise-induced hearing loss as a result of adaptive changes in central auditory pathways from brainstem to auditory cortex. Kv3.1 channels are expressed in many of these circuits and, along with another Kv3 channel subtype, the Kv3.2 channel, also contribute to the function of GABAergic inhibitory interneurons that may control the function of mid-brain and cortical circuits involved in auditory processing.

These data support the hypothesis that modulation of Kv3.1, Kv3.2, and/or Kv3.3 channels on neurons of the central auditory pathways could have a therapeutic benefit in patients suffering from permanent hearing loss caused by noise exposure.

Patent applications WO2011/069951, WO2012/076877 and WO2012/168710 (application number PCT/GB2012/051278) disclose compounds which are modulators of Kv3.1 and Kv3.2.

Thus, there is a continuing need for new methods for:
preventing or reducing the development of a permanent shift in the auditory threshold after noise exposure; and/or
preventing or reducing the development of permanent tinnitus after noise exposure; and/or
preventing or reducing the development of permanently degraded central auditory processing after noise exposure.

The present inventors have found that, surprisingly, modulation of Kv3.1, Kv3.2 and/or Kv3.3 channels in higher auditory circuits may be beneficial in preventing or limiting the establishment of a permanent hearing loss resulting from acute noise exposure. The benefits of such prevention may be observed even after administration of the pharmaceutical compounds has been ceased.

SUMMARY OF THE INVENTION

The present invention provides a compound of formula (I) or a pharmaceutically acceptable salt and/or solvate thereof and/or derivative thereof, for use in the prophylaxis of acute noise-induced hearing loss:

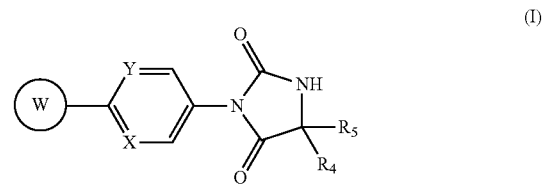

(I)

wherein:
W is group (Wa), group (Wb) or group (Wc):

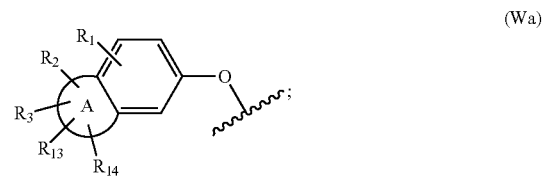

(Wa)

(Wb)

(Wc)

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;

$R_{15}$ is H or $C_{1-4}$alkyl;

$R_{16}$ is halo, $C_{1-4}$ alkyl, $C_{1-4}$ alkoxy, halo-$C_{1-4}$alkyl, halo-$C_{1-4}$alkoxy, or CN;

$R_{17}$ is H, halo, cyano, $C_{1-4}$ alkyl or $C_{1-4}$ alkoxy; with the proviso that when $R_{17}$ is H, $R_{16}$ is not in the para position;

$R_4$ is $C_{1-4}$ alkyl;

$R_5$ is H or $C_{1-4}$ alkyl;

or $R_4$ and $R_5$ can be fused to form $C_{3-4}$ spiro carbocyclyl;

wherein $R_2$ and $R_3$ may be attached to the same or a different ring atom; $R_2$ may be attached to a fused ring atom; and wherein $R_{13}$ and $R_{14}$ may be attached to the same or a different ring atom.

Also provided is a method of prophylaxis of acute noise-induced hearing loss, by administering to a subject a compound of formula (I) or a pharmaceutically acceptable salt and/or solvate thereof and/or derivative thereof, as defined above.

Further provided are compounds of formula (I) as defined above for use in the manufacture of a medicament for the prophylaxis of acute noise-induced hearing loss.

DETAILED DESCRIPTION OF THE INVENTION

The present invention provides a compound of formula (I) or a pharmaceutically acceptable salt and/or solvate thereof and/or derivative thereof, for use in the prophylaxis of acute noise-induced hearing loss:

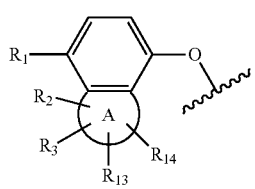

(I)

wherein:
W is group (Wa), group (Wb) or group (Wc):

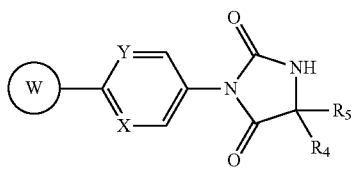

(Wa)

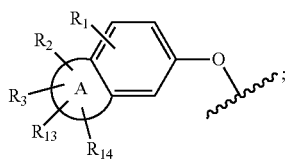

(Wb)

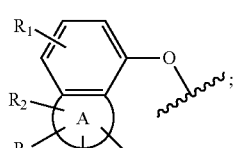

(Wc)

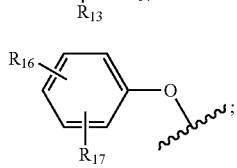

wherein:
$R_1$ is H, $C_{1-4}$alkyl, halo, halo$C_{1-4}$alkyl, CN, $C_{1-4}$alkoxy, or halo$C_{1-4}$alkoxy;

$R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

X is CH or N;

Y is $CR_{15}$ or N;

$R_{15}$ is H or $C_{1-4}$alkyl;

$R_{16}$ is halo, $C_{1-4}$ alkyl, $C_{1-4}$ alkoxy, halo-$C_{1-4}$alkyl, halo-$C_{1-4}$alkoxy or CN;

$R_{17}$ is H, halo, cyano, $C_{1-4}$ alkyl or $C_{1-4}$ alkoxy; with the proviso that when $R_{17}$ is H, $R_{16}$ is not in the para position;

$R_4$ is $C_{1-4}$ alkyl;

$R_5$ is H or $C_{1-4}$ alkyl;

or $R_4$ and $R_5$ can be fused to form $C_{3-4}$ spiro carbocyclyl;

wherein $R_2$ and $R_3$ may be attached to the same or a different ring atom; $R_2$ may be attached to a fused ring atom; and wherein $R_{13}$ and $R_{14}$ may be attached to the same or a different ring atom.

The present invention also provides a method of prophylaxis of acute noise-induced hearing loss, by administering to a subject a compound of formula (I) or a pharmaceutically acceptable salt and/or solvate thereof and/or derivative thereof.

The present invention also provides a compound of formula (I) or a pharmaceutically acceptable salt and/or solvate thereof and/or derivative thereof, for use in the manufacture of a medicament for the prophylaxis of acute noise-induced hearing loss.

The compounds of formula (I) may optionally be utilised in the form of a pharmaceutically acceptable salt and/or solvate. In one embodiment of the invention a compound of formula (I) is utilised in the form of a pharmaceutically acceptable salt. In a second embodiment of the invention a compound of formula (I) is utilised in the form of a pharmaceutically acceptable solvate. In a third embodiment of the invention a compound of formula (I) is not in the form of a salt or solvate.

Suitably, $R_1$ is H, $C_{1-4}$alkyl, halo or halo$C_{1-4}$alkyl. In another embodiment of the invention $R_1$ is H or methyl. In one embodiment of the invention $R_1$ is H. In another embodiment of the invention $R_1$ is $C_{1-4}$alkyl, in particular methyl. When W is group (Wa), suitably $R_1$ is H. When W is group (Wb), suitably $R_1$ is H or methyl.

When W is group (Wb), suitably $R_1$ is positioned at the para position of the phenyl ring, as illustrated below:

Suitably $R_2$ is H, $C_{1-4}$alkyl, $C_{3-5}$-spiro carbocyclyl, or halo$C_{1-4}$alkyl. In one embodiment of the invention $R_2$ is $C_{1-4}$alkyl, in particular methyl, ethyl, isopropyl, tert-butyl or cyclopropyl, especially methyl, ethyl, isopropyl or tert-butyl. In one embodiment of the invention $R_2$ is $C_{3-5}$-spiro carbocyclyl. In one embodiment of the invention $R_2$ is $C_3$-spiro carbocyclyl. In another embodiment of the invention $R_2$ is $C_4$ spiro carbocyclyl. In a further embodiment of the invention $R_2$ is $C_5$-spiro carbocyclyl. In one embodiment of the invention $R_2$ is halo$C_{1-4}$alkyl, in particular trifluoromethyl or 2,2,2-trifluoroethyl. In one embodiment of the invention $R_2$ is halo, in particular fluoro. In another embodiment of the invention $R_2$ is H.

In one embodiment of the invention $R_3$ is H, $C_{1-4}$alkyl, halo$C_{1-4}$alkyl or halo. Alternatively, $R_3$ is H, $C_{1-4}$alkyl, or halo$C_{1-4}$alkyl. Suitably $R_3$ is H or $C_{1-4}$alkyl. In one embodiment of the invention $R_3$ is H. In one embodiment of the invention $R_3$ is $C_{1-4}$alkyl, in particular methyl, ethyl, isopropyl, tert-butyl or cyclopropyl, especially methyl, ethyl, isopropyl or tert-butyl, such as methyl or ethyl. In one embodiment of the invention, $R_3$ is halo$C_{1-4}$alkyl, in particular trifluoromethyl or 2,2,2-trifluoroethyl. In one embodiment of the invention $R_3$ is halo, in particular fluoro. The skilled person will appreciate that, depending on the size, presence of heteroatoms and the degree of unsaturation of the A ring, $R_3$ may be absent. Consequently, in another embodiment of the invention $R_3$ is absent. Suitably $R_3$ is H, methyl or trifluoromethyl.

In one embodiment of the invention $R_2$ may be H, $C_{1-4}$alkyl, halo$C_{1-4}$alkyl or $C_{3-5}$-spiro carbocyclyl and $R_3$ may be H, $C_{1-4}$alkyl, or halo$C_{1-4}$alkyl. In a particular embodiment of the invention, $R_2$ may be methyl, ethyl, isopropyl, tert-butyl, cyclopropyl, $C_{3-5}$-spiro carbocyclyl, trifluoromethyl or 2,2,2-trifluoroethyl and $R_3$ may be H, methyl, ethyl or trifluoromethyl. In certain embodiments of the invention $R_3$ is H and $R_2$ is H, methyl, ethyl, isopropyl or $C_{3-4}$ spiro carbocyclyl. In further embodiments of the invention $R_3$ and $R_2$ are both fluoro (such as attached to the same ring carbon atom). In one embodiment of the invention $R_2$ is $C_{1-4}$alkyl and $R_3$ is H, for example $R_2$ is methyl, ethyl, tert-butyl or cyclopropyl. In one embodiment of the invention $R_2$ is $C_{1-4}$alkyl and $R_3$ is $C_{1-4}$alkyl, for example $R_2$ is methyl and $R_3$ is methyl, $R_2$ is ethyl and $R_3$ is ethyl or $R_2$ is methyl and $R_3$ is ethyl. In another embodiment of the invention $R_2$ is trifluoromethyl and $R_3$ is methyl.

In one embodiment of the invention $R_2$ and $R_3$ are attached to the same ring atom. In an alternative embodiment of the invention $R_2$ and $R_3$ are attached to different ring atoms.

In one embodiment of the invention $R_{13}$ is H, F or methyl. In one embodiment of the invention $R_{13}$ is H. In another embodiment of the invention $R_{13}$ is $C_{1-4}$alkyl, in particular methyl. In a further embodiment of the invention $R_{13}$ is halo, in particular fluoro. In an additional embodiment of the invention $R_{13}$ is halo$C_{1-4}$alkyl, such as trifluoromethyl. The skilled person will appreciate that, depending on the size, presence of heteroatoms and the degree of unsaturation of the A ring, $R_{13}$ may be absent. Consequently, in another embodiment of the invention $R_{13}$ is absent.

In one embodiment of the invention $R_{14}$ is H, F or methyl. In one embodiment of the invention $R_{14}$ is H. In another embodiment of the invention $R_{14}$ is $C_{1-4}$alkyl, in particular methyl. In a further embodiment of the invention $R_{14}$ is halo, in particular fluoro. In an additional embodiment of the invention $R_{13}$ is halo$C_{1-4}$alkyl, such as trifluoromethyl. The skilled person will appreciate that, depending on the size, presence of heteroatoms and the degree of unsaturation of the A ring, $R_{14}$ may be absent. Consequently, in another embodiment of the invention $R_{14}$ is absent.

In one embodiment of the invention $R_{13}$ and $R_{14}$ are attached to the same ring atom. In an alternative embodiment of the invention $R_{13}$ and $R_{14}$ are attached to different ring atoms.

In certain embodiments of the invention $R_2$, $R_3$, $R_{13}$ and $R_{14}$ are each independently selected from H, $C_{1-4}$alkyl, halo$C_{1-4}$alkyl and halo, such as H, $C_{1-4}$alkyl and halo$C_{1-4}$alkyl. Suitably $R_2$, $R_3$, $R_{13}$ and $R_{14}$ are each independently selected from H, F, methyl and trifluoromethyl.

Suitably, A is a 5 or 6 membered saturated or unsaturated heterocycle, with at least one O atom; which heterocycle is optionally fused with a cyclopropyl group to form a tricycle when considered together with the phenyl. In one embodiment of the invention A is a 5 membered saturated or unsaturated heterocycle, with at least one O atom; which heterocycle is optionally fused with a cyclopropyl group, a cyclobutyl group or a cyclopentyl group to form a tricycle when considered together with the phenyl. In another embodiment of the invention A is a 6 membered saturated or unsaturated heterocycle, with at least one O atom; which heterocycle is optionally fused with a cyclopropyl group, a cyclobutyl group or a cyclopentyl group to form a tricycle when considered together with the phenyl.

In one embodiment of the invention A is a 5 membered saturated or unsaturated heterocycle with at least one O atom, which heterocycle is fused with a cyclopropyl group to form a tricycle when considered together with the phenyl. In another embodiment of the invention A is a 6 membered saturated or unsaturated heterocycle with at least one O atom, which heterocycle is fused with a cyclopropyl group to form a tricycle when considered together with the phenyl. In one embodiment of the invention A is a 5 membered saturated or unsaturated heterocycle with at least one O atom. In one embodiment of the invention A is a 6 membered saturated or unsaturated heterocycle with at least one O atom.

In certain embodiments of the invention the ring A contains one heteroatom. In other embodiments of the invention the ring A contains two heteroatoms (e.g. two oxygen atoms, one oxygen atom and one nitrogen atom, or one oxygen atom and one sulphur atom), in particular two oxygen atoms or one oxygen atom and one nitrogen atom.

Suitably, A is dihydrofuran, isoxazole, dihydropyran, 1,3-dioxolane, 1,3-oxazine or dihydropyran fused with a cyclopropyl group.

In one embodiment of the invention A is dihydrofuran. In one embodiment of the invention A is dihydropyran. In another embodiment of the invention A is dihydrofuran fused with a cyclopropyl group, a cyclobutyl group or a cyclopentyl group. In another embodiment of the invention A is dihydropyran fused with a cyclopropyl group, a cyclobutyl group or a cyclopentyl group. In a further embodiment the invention A is dihydrofuran fused with a cyclopropyl group. In still further embodiment the invention A is dihydropyran fused with a cyclopropyl group.

In one embodiment of the invention A is fused with a cyclopropyl group. In another embodiment A is fused with a cyclobutyl group. In a further embodiment of the invention A is fused with a cyclopentyl group. In one embodiment of the invention A is not fused with a cyclopropyl group, a cyclobutyl group or a cyclopentyl group.

In one embodiment of the invention W is group (Wa):

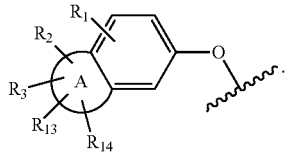
(Wa)

In one embodiment of the invention W is group (Wb):

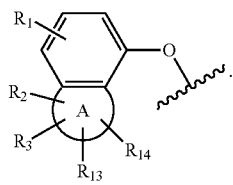
(Wb)

In one embodiment of the invention A is dihydrofuran, dihydropyran, furan, pyran, oxazole, isoxazole, oxazine, dioxine or 1,3-dioxalane. In another embodiment A is dihydrofuran, dihydropyran or 1,3-dioxalane.

In one embodiment of the invention A is:

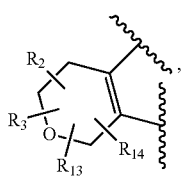
1

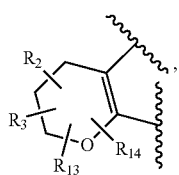
2

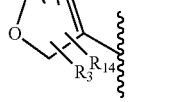
3

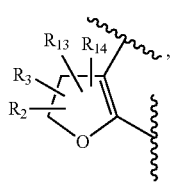
4

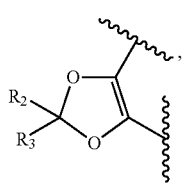
5

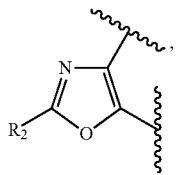
6

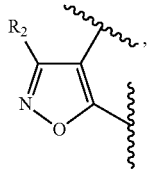
7

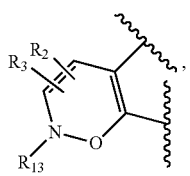
8

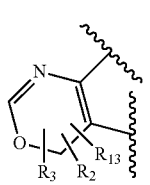
9 or

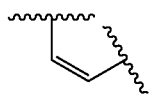 [SMILES: */C=C\*]
10 wherein

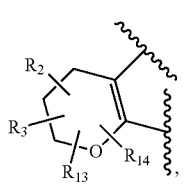

denotes a portion of the phenyl ring to which ring A is fused.

In another embodiment of the invention A is:

1

2

-continued

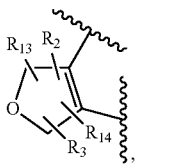
3

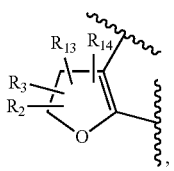
4

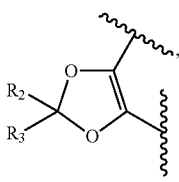
5

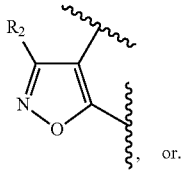
7

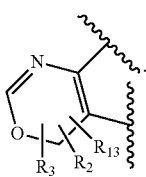
10 wherein

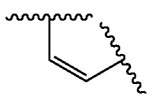

denotes a portion of the phenyl ring to which ring A is fused.

In a further embodiment of the invention A is:

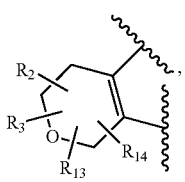
1

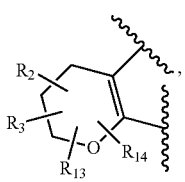
2

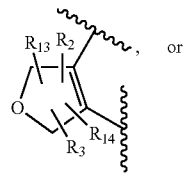
3

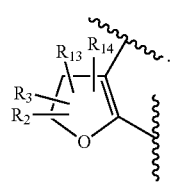
4 wherein

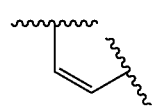

denotes a portion of the phenyl ring to which ring A is fused.

When A contains a 5 membered heterocycle containing one oxygen atom, suitably the heterocycle is dihydrofuran.

When A is a 5 membered heterocycle containing one oxygen atom, suitably the oxygen atom is located at the benzylic position relative to the phenyl ring.

When W is group (Wa), suitably A is a 5 membered heterocycle containing one heteroatom, wherein the oxygen atom is located at the benzylic or para position relative to the phenyl ring.

When W is group (Wb), suitably A is a 5 membered heterocycle containing one heteroatom, wherein the oxygen atom is located at the benzylic or meta position relative to the phenyl ring.

When W is group (Wa), in one embodiment of the invention, group (Wa) is:

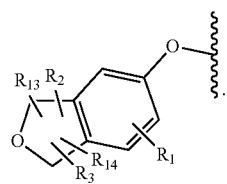
11

When W is group (Wa), in another embodiment or the invention, group (Wa) is:

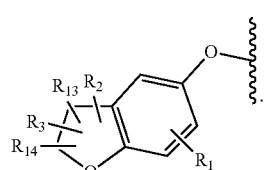
12

When W is group (Wb), in one embodiment of the invention, group (Wb) is:

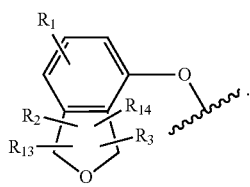

13

When W is group (Wb), in another embodiment of the invention, (Wb) is:

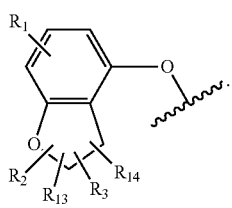

14

When W is group (Wb) in a further embodiment of the invention, group (Wb) is:

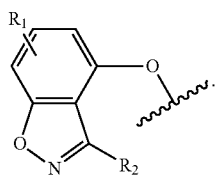

15

When A contains a 6 membered heterocycle containing one oxygen atom, suitably the heterocycle is dihydropyran.

When W is group (Wa), suitably A is a 6 membered heterocycle containing one oxygen atom, wherein the oxygen atom is located at the para position relative to the phenyl ring.

When W is group (Wb), suitably A contains a 6 membered heterocycle containing one oxygen atom, wherein the oxygen atom is located at the meta position relative to the phenyl ring.

When W is group (Wa), in one embodiment of the invention, group (Wa) is:

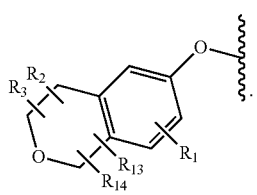

16

When W is group (Wa), in another embodiment of the invention, group (Wa) is:

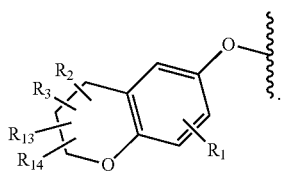

17

When W is group (Wb), in one embodiment of the invention, group (Wb) is:

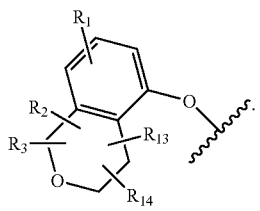

18

When W is group (Wb), in one embodiment of the invention, group (Wb) is:

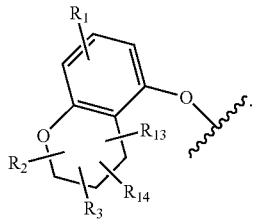

19

When W is group (Wb), in one embodiment of the invention, group (Wb) is:

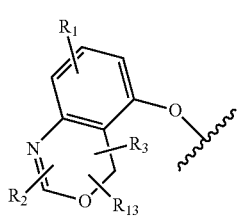

20

When W is group (Wa), in one embodiment of the invention, A is:

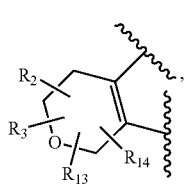

1

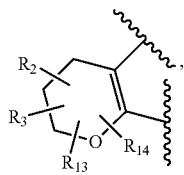

2

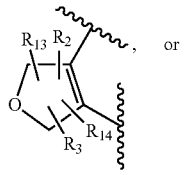

3 or

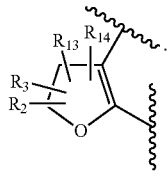

4

When W is group (Wa), in one embodiment of the invention, A is:

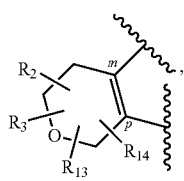

21

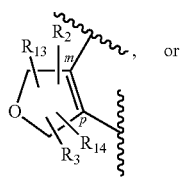

22 or

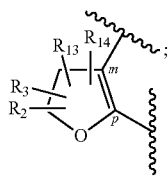

23 wherein m and p denote the meta and para positions, respectively, of ring A relative to the phenyl ring.

When W is group (Wa), in a further embodiment of the invention, A is selected from the group consisting of:

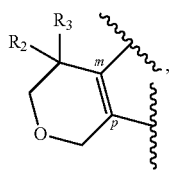

24

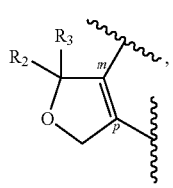

25

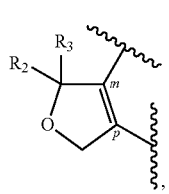

26 and

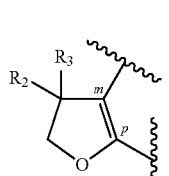

27 wherein m and p denote the meta and para positions, respectively, of ring A relative to the phenyl ring.

When W is group (Wb), in one embodiment of the invention, A is:

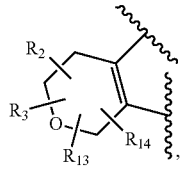

1

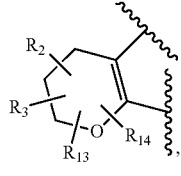

2

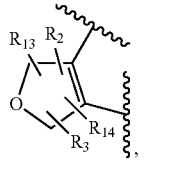

3

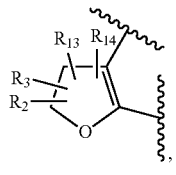

4

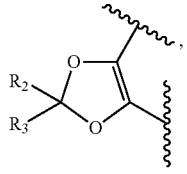

5

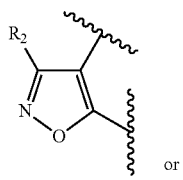 or
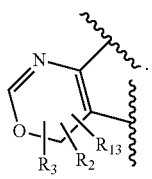
When W is group (Wb), in one embodiment of the invention, A is:
28
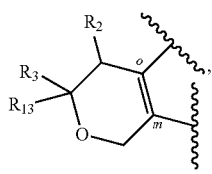
29
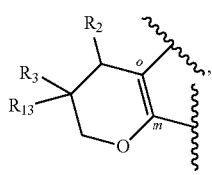
30
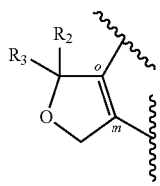
31
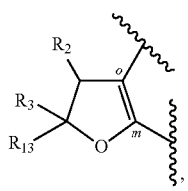
5
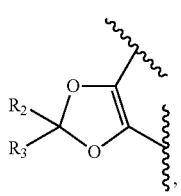
32
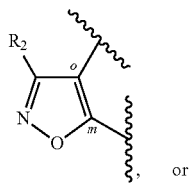 or
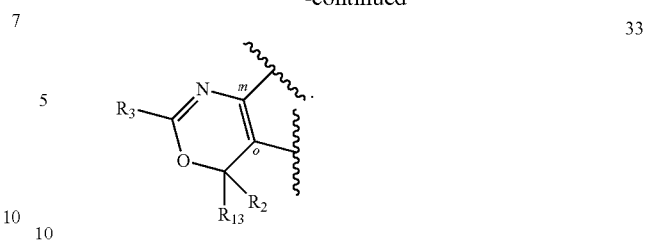
When W is group (Wb), in one embodiment of the invention, A is:
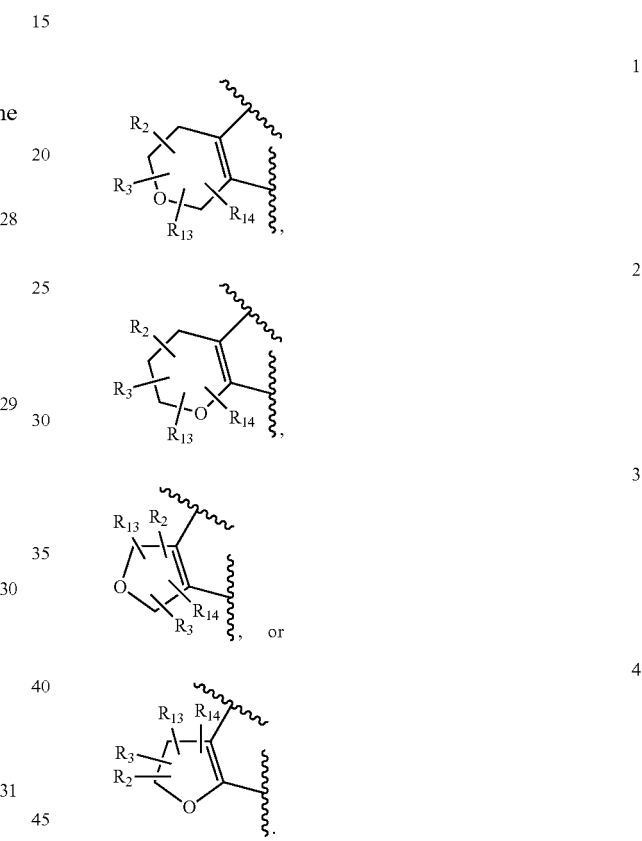
When W is group (Wb), in another embodiment of the invention, A is:
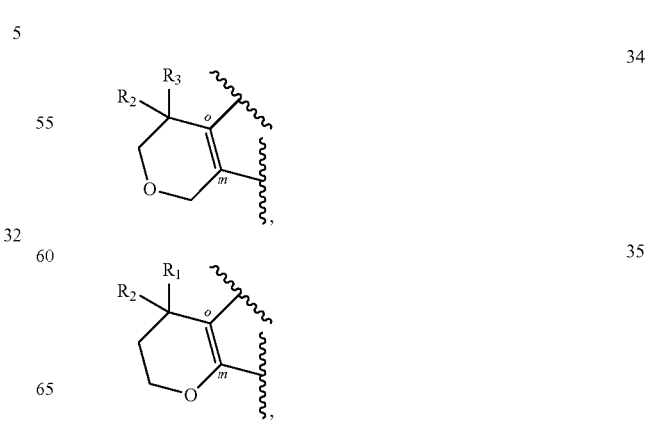

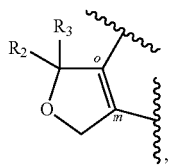

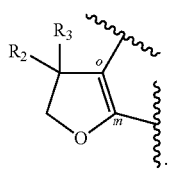

In one embodiment W is the group Wc.

When W is group (Wc), in one embodiment of the invention $R_{16}$ is $C_{1-4}$alkoxy. In another embodiment of the invention $R_{16}$ is methoxy. In one embodiment of the invention $R_{16}$ is $C_{1-4}$alkyl. In another embodiment of the invention $R_{16}$ is methyl. In a further embodiment of the invention $R_{16}$ is ethyl. In a yet further embodiment of the invention $R_{16}$ is propyl. In a yet further embodiment of the invention $R_{16}$ is butyl. In one embodiment of the invention $R_{16}$ is halo. In another embodiment of the invention $R_{16}$ is chloro. In a further embodiment of the invention $R_{16}$ is fluoro. In one embodiment of the invention $R_{16}$ is halo-$C_{1-4}$alkoxy. In another embodiment of the invention $R_{16}$ is trifluoromethoxy. In one embodiment of the invention $R_{16}$ is halo-$C_{1-4}$alkyl. In another embodiment of the invention $R_{16}$ is trifluoromethyl. In one embodiment of the invention $R_{16}$ is cyano.

In one embodiment of the invention, $R_{17}$ is H. In one embodiment of the invention $R_{17}$ is $C_{1-4}$alkyl. In another embodiment of the invention $R_{17}$ is methyl. In one embodiment of the invention $R_{17}$ is halo. In another embodiment of the invention, $R_{17}$ is chloro. In a further embodiment of the invention $R_{17}$ is fluoro. In one embodiment of the invention $R_{17}$ is $C_{1-4}$alkyl. In one embodiment of the invention $R_{17}$ is cyano.

In one embodiment of the invention $R_{16}$ is $C_{1-4}$alkyl, $C_{1-4}$alkoxy, or halo-$C_{1-4}$alkoxy; $R_{17}$ is H, cyano or alkyl; X is N, Y is N or $CR_{15}$, $R_4$ is $C_{1-4}$alkyl, and $R_5$ is $C_{1-4}$alkyl or H. In one embodiment of the invention $R_{16}$ is propyl, butyl, methoxy, propoxy, or trifluoromethoxy; $R_{17}$ is H, cyano or methyl; X is N, Y is N or $CR_{15}$, $R_4$ is ethyl, and $R_5$ is methyl or H.

In one embodiment, one of $R_{16}$ and $R_{17}$ is in the para position and the remaining $R_{16}$ or $R_{17}$ is in the meta position. In one embodiment, one of $R_{16}$ and $R_{17}$ is in the para position and the remaining $R_{16}$ or $R_{17}$ is in the ortho position.

In one embodiment of the invention $R_{16}$ is $C_{1-4}$alkoxy and $R_{17}$ is $C_{1-4}$alkyl. In one embodiment of the invention $R_{16}$ is methoxy and $R_{17}$ is methyl. In one embodiment of the invention $R_{16}$ is $C_{1-4}$alkoxy in the meta position and $R_{17}$ is $C_{1-4}$alkyl in the para position. In a further embodiment of the invention $R_{16}$ is methoxy in the meta position, $R_{17}$ is methyl in the para position, $R_4$ is $C_{1-4}$alkyl, $R_5$ is H, $R_4$ is in the R configuration. In a yet further embodiment of the invention $R_{16}$ is methoxy in the meta position, $R_{17}$ is methyl in the para position, X is N, Y is C, $R_4$ is $C_{1-4}$alkyl, $R_5$ is H and the absolute configuration of the stereogenic centre is R. In a still further embodiment of the invention $R_{16}$ is methoxy in the meta position, $R_{17}$ is methyl in the para position, X is N, Y is C, $R_4$ is ethyl, $R_5$ is H and the absolute configuration of the stereogenic centre is R.

Suitably, $R_4$ is methyl, ethyl, isopropyl or t-butyl. In one embodiment of the invention $R_4$ is methyl. In another embodiment of the invention $R_4$ is ethyl. In a further embodiment of the invention $R_4$ is propyl, such is isopropyl. In a yet further embodiment of the invention $R_4$ is butyl, such as t-butyl.

Suitably, $R_5$ is H or methyl. In one embodiment of the invention $R_5$ is H. In a second embodiment of the invention $R_5$ is $C_{1-4}$alkyl, in particular $R_5$ is methyl.

In one embodiment of the invention $R_4$ and $R_5$ together form a $C_3$ spiro carbocycle. In a second embodiment of the invention $R_4$ and $R_5$ together form a $C_4$ spiro carbocycle. In a further embodiment of the invention $R_4$ is methyl and $R_5$ is methyl. In an embodiment of particular interest, $R_4$ is ethyl and $R_5$ is methyl. In another embodiment, $R_4$ is ethyl and $R_5$ is ethyl. In an additional embodiment, $R_4$ is ethyl and $R_5$ is H.

Suitably, $R_4$ and $R_5$ have the stereochemical arrangement:

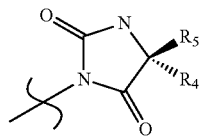

In one embodiment of the invention X is CH. In another embodiment of the invention X is N.

In one embodiment of the invention Y is $CR_{15}$. In another embodiment of the invention Y is N. In a further embodiment of the invention Y is $CR_{15}$, wherein $R_{15}$ is H. In a still further embodiment of the invention Y is $CR_{15}$, wherein $R_{15}$ is $C_{1-4}$alkyl, in particular methyl.

In one embodiment of the invention X is CH and Y is $CR_{15}$, wherein $R_{15}$ is H. In another embodiment of the invention X is N and Y is $CR_{15}$, wherein $R_{15}$ is H. In a further embodiment of the invention X is N and Y is $CR_{15}$, wherein $R_{15}$ is methyl. In a further embodiment of the invention X is CH and Y is $CR_{15}$, wherein $R_{15}$ is methyl. In a still further embodiment of the invention X is N and Y is N.

When W is group (Wc), suitably the compound of formula (I) is selected from:
(5R)-5-methyl-3-{4-[(3-methylphenyl)oxy]phenyl}-2,4-imidazolidinedione;
(5R)-5-methyl-3-(4-{[3-(methyloxy)phenyl]oxy}phenyl)-2,4-imidazolidinedione;
(5R)-3-(4-{[3-(ethyloxy)phenyl]oxy}phenyl)-5-methyl-2,4-imidazolidinedione;
(5R)-3-{4-[(3-chloro-5-fluorophenyl)oxy]phenyl}-5-methyl-2,4-imidazolidinedione;
(5R)-3-{4-[(3-chloro-4-fluorophenyl)oxy]phenyl}-5-methyl-2,4-imidazolidinedione;
(5S)-3-{4-[(3-chloro-4-fluorophenyl)oxy]phenyl}-5-methyl-2,4-imidazolidinedione;
(5R)-5-methyl-3-(4-{[2-methyl-5-(methyloxy)phenyl]oxy}phenyl)-2,4-imidazolidinedione;
(5R)-5-methyl-3-(4-{[4-methyl-3-(methyloxy)phenyl]oxy}phenyl)-2,4-imidazolidinedione;
(5R)-5-methyl-3-(6-{[3-(1-methylethyl)phenyl]oxy}-3-pyridinyl)-2,4-imidazolidinedione;
(5R)-5-methyl-3-[6-({3-[(1-methylethyl)oxy]phenyl}oxy)-3-pyridinyl]-2,4-imidazolidinedione;

(5R)-3-{6-[(2,5-dimethylphenyl)oxy]-3-pyridinyl}-5-methyl-2,4-imidazolidinedione;
(5R)-3-{6-[(2,3-dimethylphenyl)oxy]-3-pyridinyl}-5-methyl-2,4-imidazolidinedione;
(5R)-3-{6-[(2,6-dimethylphenyl)oxy]-3-pyridinyl}-5-methyl-2,4-imidazolidinedione;
(5R)-3-{6-[(2-ethylphenyl)oxy]-3-pyridinyl}-5-methyl-2,4-imidazolidinedione;
(5R)-5-methyl-3-(6-{[4-methyl-3-(methyloxy)phenyl]oxy}-3-pyridinyl)-2,4-imidazolidinedione;
(5R)-5-methyl-3-(6-{[2-methyl-5-(methyloxy)phenyl]oxy}-3-pyridinyl)-2,4-imidazolidinedione;
(5R)-5-methyl-3-(6-{[2-methyl-3-(methyloxy)phenyl]oxy}-3-pyridinyl)-2,4-imidazolidinedione;
(5R)-5-ethyl-3-(4-{[3-(methyloxy)phenyl]oxy}phenyl)-2,4-imidazolidinedione;
(5R)-5-ethyl-3-(6-{[4-methyl-3-(methyloxy)phenyl]oxy}-3-pyridinyl)-2,4-imidazolidinedione;
(5S)-5-ethyl-3-(6-{[4-methyl-3-(methyloxy)phenyl]oxy}-3-pyridinyl)-2,4-imidazolidinedione;
(5R)-5-ethyl-3-(6-{[3-(1-methylethyl)phenyl]oxy}-3-pyridinyl)-2,4-imidazolidinedione;
5,5-dimethyl-3-(4-{[3-(methyloxy)phenyl]oxy}phenyl)-2,4-imidazolidinedione;
3-{4-[(2,3-dimethylphenyl)oxy]phenyl}-5,5-dimethyl-2,4-imidazolidinedione;
3-{6-[(2-ethylphenyl)oxy]-3-pyridinyl}-5,5-dimethyl-2,4-imidazolidinedione;
3-{6-[(2,6-dimethylphenyl)oxy]-3-pyridinyl}-5,5-dimethyl-2,4-imidazolidinedione;
(5R)-5-(1-methylethyl)-3-(4-{[4-methyl-3-(methyloxy)phenyl]oxy}phenyl)-2,4-imidazolidinedione;
(5R)-5-methyl-3-(2-{[3-(1-methylethyl)phenyl]oxy}-5-pyrimidinyl)-2,4-imidazolidinedione;
(5R)-5-ethyl-3-(2-{[3-(ethyloxy)-4-methylphenyl]oxy}-5-pyrimidinyl)-2,4-imidazolidinedione;
(5R)-5-(1,1-dimethylethyl)-3-(6-{[4-methyl-3-(methyloxy)phenyl]oxy}-3-pyridinyl)-2,4-imidazolidinedione;
(5R)-5-ethyl-5-methyl-3-(6-{[4-methyl-3-(methyloxy)phenyl]oxy}-3-pyridinyl)-2,4-imidazolidinedione;
7-(6-{[4-methyl-3-(methyloxy)phenyl]oxy}-3-pyridinyl)-5,7-diazaspiro[3.4]octane-6,8-dione;
6-(6-{[4-methyl-3-(methyloxy)phenyl]oxy}-3-pyridinyl)-4,6-diazaspiro[2.4]heptane-5,7-dione;
4-{[5-(4,4-dimethyl-2,5-dioxo-1-imidazolidinyl)-2-pyridinyl]oxy}-2-(1-methylethyl)benzonitrile;
4-{[5-(4,4-dimethyl-2,5-dioxo-1-imidazolidinyl)-2-pyridinyl]oxy}-2-[(trifluoromethyl)oxy]benzonitrile;
3-{6-[(4-fluoro-3-methylphenyl)oxy]-3-pyridinyl}-5,5-dimethyl-2,4-imidazolidinedione;
3-{6-[(4-fluoro-2-methylphenyl)oxy]-3-pyridinyl}-5,5-dimethyl-2,4-imidazolidinedione;
5,5-dimethyl-3-(6-{[4-methyl-3-(methyloxy)phenyl]oxy}-3-pyridinyl)-2,4-imidazolidinedione;
(5R)-5-(1-methylethyl)-3-(6-{[4-methyl-3-(methyloxy)phenyl]oxy}-3-pyridinyl)-2,4-imidazolidinedione;
3-(6-{[2-(1,1-dimethylethyl)phenyl]oxy}-3-pyridinyl)-5,5-dimethyl-2,4-imidazolidinedione;
3-(2-{[2-(1,1-dimethylethyl)phenyl]oxy}-5-pyrimidinyl)-5,5-dimethyl-2,4-imidazolidinedione;
(5R)-5-ethyl-5-methyl-3-(2-{[4-methyl-3-(methyloxy)phenyl]oxy}-5-pyrimidinyl)-2,4-imidazolidinedione;
(5R)-5-ethyl-3-(2-{[3-(ethyloxy)-4-methylphenyl]oxy}-5-pyrimidinyl)-5-methyl-2,4-imidazolidinedione;
5,5-dimethyl-3-[6-({3-[(trifluoromethyl)oxy]phenyl}oxy)-3-pyridinyl]-2,4-imidazolidinedione;
4-{[5-(4,4-dimethyl-2,5-dioxo-1-imidazolidinyl)-2-pyridinyl]oxy}-3-ethylbenzonitrile;
2-chloro-4-{[5-(4,4-dimethyl-2,5-dioxo-1-imidazolidinyl)-2-pyridinyl]oxy}benzonitrile;
5,5-dimethyl-3-[6-({4-methyl-3-[(trifluoromethyl)oxy]phenyl}oxy)-3-pyridinyl]-2,4-imidazolidinedione;
4-{[5-(4,4-dimethyl-2,5-dioxo-1-imidazolidinyl)-2-pyridinyl]oxy}-2-(methyloxy)benzonitrile;
4-{[5-(4,4-dimethyl-2,5-dioxo-1-imidazolidinyl)-2-pyridinyl]oxy}-3-methylbenzonitrile;
4-{[5-(4,4-dimethyl-2,5-dioxo-1-imidazolidinyl)-2-pyridinyl]oxy}-3-(trifluoromethyl)benzonitrile;
4-{[5-(4,4-dimethyl-2,5-dioxo-1-imidazolidinyl)-2-pyridinyl]oxy}-2-ethylbenzonitrile;
4-{[5-(4,4-dimethyl-2,5-dioxo-1-imidazolidinyl)-2-pyrimidinyl]oxy}-2-ethylbenzonitrile;
3-cyclopropyl-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-3-(1,1-dimethylethyl)benzonitrile;
2-[(cyclopropylmethyl)oxy]-4-{[5-(4,4-dimethyl-2,5-dioxo-1-imidazolidinyl)-2-pyridinyl]oxy}benzonitrile;
4-{[5-(4,4-dimethyl-2,5-dioxo-1-imidazolidinyl)-2-pyridinyl]oxy}-2-(ethyloxy)benzonitrile;
2-cyclopropyl-4-{[5-(4,4-dimethyl-2,5-dioxo-1-imidazolidinyl)-2-pyridinyl]oxy}benzonitrile;
5,5-dimethyl-3-[2-({4-methyl-3-[(trifluoromethyl)oxy]phenyl}oxy)-5-pyrimidinyl]-2,4-imidazolidinedione;
4-{[5-(4,4-dimethyl-2,5-dioxo-1-imidazolidinyl)-2-pyrimidinyl]oxy}-3-(1,1-dimethylethyl)benzonitrile;
4-{[5-(4,4-dimethyl-2,5-dioxo-1-imidazolidinyl)-2-pyridinyl]oxy}-2-[(1-methylethyl)oxy]benzonitrile;
4-({5-[(4R)-4-ethyl-4-methyl-2,5-dioxo-1-imidazolidinyl]-2-pyridinyl}oxy)-2-[(1-methylethyl)oxy]benzonitrile;
3-cyclopropyl-4-({5-[(4R)-4-ethyl-4-methyl-2,5-dioxo-1-imidazolidinyl]-2-pyridinyl}oxy)benzonitrile;
4-({5-[(4R)-4-ethyl-4-methyl-2,5-dioxo-1-imidazolidinyl]-2-pyridinyl}oxy)-2-[(trifluoromethyl)oxy]benzonitrile;
2-cyclopropyl-4-({5-[(4R)-4-ethyl-4-methyl-2,5-dioxo-1-imidazolidinyl]-2-pyridinyl}oxy)benzonitrile;
(5R)-5-ethyl-5-methyl-3-[2-({4-methyl-3-[(trifluoromethyl)oxy]phenyl}oxy)-5-pyrimidinyl]-2,4-imidazolidinedione;
3-(1,1-dimethylethyl)-4-({5-[(4R)-4-ethyl-4-methyl-2,5-dioxo-1-imidazolidinyl]-2-pyrimidinyl}oxy)benzonitrile;
3-(1,1-dimethylethyl)-4-({5-[(4R)-4-ethyl-4-methyl-2,5-dioxo-1-imidazolidinyl]-2-pyridinyl}oxy)benzonitrile;
4-{[4-(4,4-dimethyl-2,5-dioxo-1-imidazolidinyl)phenyl]oxy}-2-(methyloxy)benzonitrile;
4-{[4-(4,4-dimethyl-2,5-dioxo-1-imidazolidinyl)phenyl]oxy}-2-(ethyloxy)benzonitrile;
4-({4-[(4R)-4-ethyl-2,5-dioxo-1-imidazolidinyl]phenyl}oxy)-2-(ethyloxy)benzonitrile;
3-cyclopropyl-4-({5-[(4R)-4-ethyl-2,5-dioxo-1-imidazolidinyl]-2-pyridinyl}oxy)benzonitrile;
3-(1,1-dimethylethyl)-4-({5-[(4R)-4-ethyl-2,5-dioxo-1-imidazolidinyl]-2-pyridinyl}oxy)benzonitrile;
4-({5-[(4R)-4-ethyl-2,5-dioxo-1-imidazolidinyl]-2-pyridinyl}oxy)-2-(methyloxy)benzonitrile;
4-({4-[(4R)-4-ethyl-2,5-dioxo-1-imidazolidinyl]phenyl}oxy)-2-(methyloxy)benzonitrile;
2-[(cyclopropylmethyl)oxy]-4-({5-[(4R)-4-ethyl-2,5-dioxo-1-imidazolidinyl]-2-pyridinyl}oxy)benzonitrile;
(5R)-5-ethyl-3-[6-({4-methyl-3-[(trifluoromethyl)oxy]phenyl}oxy)-3-pyridinyl]-2,4-imidazolidinedione;
2-cyclopropyl-4-({5-[(4R)-4-ethyl-2,5-dioxo-1-imidazolidinyl]-2-pyridinyl}oxy)benzonitrile;

4-({5-[(4R)-4-ethyl-2,5-dioxo-1-imidazolidinyl]-2-pyridinyl}oxy)-2-(1-methylethyl)benzonitrile;
4-({5-[(4R)-4-ethyl-2,5-dioxo-1-imidazolidinyl]-2-pyridinyl}oxy)-2-(1-methylethyl)benzonitrile;
(5R)-5-ethyl-3-[2-({4-methyl-3-[(trifluoromethyl)oxy]phenyl}oxy)-5-pyrimidinyl]-2,4-imidazolidinedione;
4-({5-[(4R)-4-ethyl-2,5-dioxo-1-imidazolidinyl]-2-pyridinyl}oxy)-2-[(1-methylethyl)oxy]benzonitrile;
4-({5-[(4R)-4-ethyl-2,5-dioxo-1-imidazolidinyl]-2-pyridinyl}oxy)-3-methylbenzonitrile;
4-({5-[(4R)-4-ethyl-2,5-dioxo-1-imidazolidinyl]-2-pyridinyl}oxy)-2-[(trifluoromethyl)oxy]benzonitrile;
3-ethyl-4-({5-[(4R)-4-ethyl-2,5-dioxo-1-imidazolidinyl]-2-pyrimidinyl}oxy)benzonitrile;
4-({5-[(4R)-4-ethyl-2,5-dioxo-1-imidazolidinyl]-2-pyrimidinyl}oxy)-3-methylbenzonitrile;
3-(1,1-dimethylethyl)-4-({5-[(4R)-4-ethyl-2,5-dioxo-1-imidazolidinyl]-2-pyrimidinyl}oxy)benzonitrile and
4-({5-[(4R)-4-ethyl-4-methyl-2,5-dioxo-1-imidazolidinyl]-2-pyridinyl}oxy)-2-(1-methylethyl)benzonitrile;
or a pharmaceutically acceptable salt and/or solvate thereof and/or derivative thereof.

When W is group (Wb), suitably the compound of formula (I) is selected from:
(5R)-3-[4-(1,3-dihydro-2-benzofuran-4-yloxy)phenyl]-5-methyl-2,4-imidazolidinedione;
(5R)-5-methyl-3-{4-[(3-methyl-1,2-benzisoxazol-4-yl)oxy]phenyl}-2,4-imidazolidinedione;
(5R)-3-{4-[(3,6-dimethyl-1,2-benzisoxazol-4-yl)oxy]phenyl}-5-methyl-2,4-imidazolidinedione;
5,5-dimethyl-3-{4-[(3-methyl-1,2-benzisoxazol-4-yl)oxy]phenyl}-2,4-imidazolidinedione;
(5R)-5-ethyl-3-{6-[(3-ethyl-1,2-benzisoxazol-4-yl)oxy]-3-pyridinyl}-2,4-imidazolidinedione;
(5R)-5-ethyl-3-(6-{[3-(1-methylethyl)-1,2-benzisoxazol-4-yl]oxy}-3-pyridinyl)-2,4-imidazolidinedione;
(5R)-3-{4-[(3,3-dimethyl-2,3-dihydro-1-benzofuran-4-yl)oxy]phenyl}-5-methyl-2,4-imidazolidinedione;
(5R)-3-{6-[(3,3-dimethyl-2,3-dihydro-1-benzofuran-4-yl)oxy]-3-pyridinyl}-5-methyl-2,4-imidazolidinedione;
(5R)-3-{6-[(3,3-dimethyl-2,3-dihydro-1-benzofuran-4-yl)oxy]-3-pyridinyl}-5-ethyl-2,4-imidazolidinedione;
(5R)-3-{2-[(3,3-dimethyl-2,3-dihydro-1-benzofuran-4-yl)oxy]-5-pyrimidinyl}-5-ethyl-2,4-imidazolidinedione;
7-{6-[(3,3-dimethyl-2,3-dihydro-1-benzofuran-4-yl)oxy]-3-pyridinyl}-5,7-diazaspiro[3.4]octane-6,8-dione;
6-{6-[(3,3-dimethyl-2,3-dihydro-1-benzofuran-4-yl)oxy]-3-pyridinyl}-4,6-diazaspiro[2.4]heptane-5,7-dione;
3-{6-[(3,3-dimethyl-2,3-dihydro-1-benzofuran-4-yl)oxy]-3-pyridinyl}-5,5-dimethyl-2,4-imidazolidinedione;
(5R)-3-{2-[(3,3-dimethyl-2,3-dihydro-1-benzofuran-4-yl)oxy]-5-pyrimidinyl}-5-(1,1-dimethylethyl)-2,4-imidazolidinedione;
(5R)-5-ethyl-3-[6-(spiro[1-benzofuran-3,1'-cyclopropan]-4-yloxy)-3-pyridinyl]-2,4-imidazolidinedione;
5,5-dimethyl-3-[6-(spiro[1-benzofuran-3,1'-cyclopropan]-4-yloxy)-3-pyridinyl]-2,4-imidazolidinedione;
(5R)-5-ethyl-5-methyl-3-[6-(spiro[1-benzofuran-3,1'-cyclopropan]-4-yloxy)-3-pyridinyl]-2,4-imidazolidinedione;
(5R)-5-ethyl-3-(6-{[(3S/R)-3-methyl-1,3-dihydro-2-benzofuran-4-yl]oxy}-3-pyridinyl)-2,4-imidazolidinedione (diastereoisomeric mixture);
(5R)-5-ethyl-3-{6-[(3-methyl-1,3-dihydro-2-benzofuran-4-yl)oxy]-3-pyridinyl}-2,4-imidazolidinedione (diastereoisomers 1 and 2);
(5R)-5-ethyl-3-{6-[(3-ethyl-1,3-dihydro-2-benzofuran-4-yl)oxy]-3-pyridinyl}-2,4-imidazolidinedione (diastereoisomeric mixture);
(5R)-5-ethyl-3-{6-[(3-ethyl-1,3-dihydro-2-benzofuran-4-yl)oxy]-3-pyridinyl}-2,4-imidazolidinedione (diastereoisomers 1 and 2);
5,5-dimethyl-3-{6-[(3-methyl-3,4-dihydro-2H-chromen-5-yl)oxy]-3-pyridinyl}-2,4-imidazolidinedione (racemate mixture);
5,5-dimethyl-3-{6-[(3-methyl-3,4-dihydro-2H-chromen-5-yl)oxy]-3-pyridinyl}-2,4-imidazolidinedione (enantiomers 1 and enantiomer 2);
5,5-dimethyl-3-{6-[(1a-methyl-1,1a,2,7b-tetrahydrocyclopropa[c]chromen-7-yl)oxy]-3-pyridinyl}-2,4-imidazolidinedione;
5,5-dimethyl-3-{6-[(1a-methyl-1,1a,2,7b-tetrahydrocyclopropa[c]chromen-7-yl)oxy]-3-pyridinyl}-2,4-imidazolidinedione (enantiomer 1 and enantiomer 2);
(5R)-5-ethyl-5-methyl-3-[6-(1H-spiro[2-benzopyran-4,1'-cyclopropan]-5-yloxy)-3-pyridinyl]-2,4-imidazolidinedione;
3-{2-[(3,3-dimethyl-2,3-dihydro-1-benzofuran-4-yl)oxy]-5-pyrimidinyl}-5,5-dimethyl-2,4-imidazolidinedione;
(5R)-3-{2-[(3,3-dimethyl-2,3-dihydro-1-benzofuran-4-yl)oxy]-5-pyrimidinyl}-5-(1-methylethyl)-2,4-imidazolidinedione;
(5R)-3-{6-[(2,2-dimethyl-2,3-dihydro-1-benzofuran-4-yl)oxy]-3-pyridinyl}-5-ethyl-2,4-imidazolidinedione;
5,5-dimethyl-3-[6-(1H-spiro[2-benzopyran-4,1'-cyclopropan]-5-yloxy)-3-pyridinyl]-2,4-imidazolidinedione;
(5R)-3-[2-(2,3-dihydrospiro[chromene-4,1'-cyclopropan]-5-yloxy)-5-pyrimidinyl]-5-ethyl-5-methyl-2,4-imidazolidinedione;
5,5-dimethyl-3-{6-[(4-methyl-3,4-dihydro-2H-chromen-5-yl)oxy]-3-pyridinyl}-2,4-imidazolidinedione (racemate mixture, enantiomer 1, enantiomer 2);
(5R)-5-ethyl-5-methyl-3-{6-[(3-methyl-3,4-dihydro-2H-chromen-5-yl)oxy]-3-pyridinyl}-2,4-imidazolidinedione (diastereoisomeric mixture, diastereoisomer 1, diastereoisomer 2);
(5R)-5-ethyl-5-methyl-3-[6-(1,1a,2,7b-tetrahydrocyclopropa[c]chromen-7-yloxy)-3-pyridinyl]-2,4-imidazolidinedione (diastereoisomeric mixture, diastereoisomer 1, diastereoisomer 2);
3-{6-[(3-ethyl-1,3-dihydro-2-benzofuran-4-yl)oxy]-3-pyridinyl}-5,5-dimethyl-2,4-imidazolidinedione (racemate mixture, enantiomer 1, enantiomer 2);
(5R)-5-ethyl-5-methyl-3-[2-(4-methylchroman-5-yl)oxypyrimidin-5-yl]imidazolidine-2,4-dione (diastereoisomeric mixture, diastereoisomer 1, diastereoisomer 2);
(5R)-5-ethyl-5-methyl-3-[2-(7-methylspiro[2H-benzofuran-3,1'-cyclopropane]-4-yl)oxypyrimidin-5-yl]imidazolidine-2,4-dione;
(5R)-3-[2-(3,3-dimethylisochroman-5-yl)oxypyrimidin-5-yl]-5-ethyl-5-methyl-imidazolidine-2,4-dione;
(5R)-5-ethyl-5-methyl-3-[2-(7-methylspiro[1H-isobenzofuran-3,1'-cyclobutane]-4-yl)oxypyrimidin-5-yl]imidazolidine-2,4-dione;
(5R)-5-ethyl-5-methyl-3-{2-[(3,3,7-trimethyl-2,3-dihydro-1-benzofuran-4-yl)oxy]-5-pyrimidinyl}-2,4-imidazolidinedione;
(5R)-3-{2-[(2,2-difluoro-7-methyl-1,3-benzodioxol-4-yl)oxy]-5-pyrimidinyl}-5-ethyl-5-methyl-2,4-imidazolidinedione;
(5R)-3-{2-[(2,2-difluoro-1,3-benzodioxol-4-yl)oxy]-5-pyrimidinyl}-5-ethyl-5-methyl-2,4-imidazolidinedione;

(5R)-5-ethyl-5-methyl-3-{2-[(2,4,4-trimethyl-4H-3,1-benzoxazin-5-yl)oxy]-5-pyrimidinyl}-2,4-imidazolidinedione;
5,5-dimethyl-3-[2-(7-methylspiro[2H-benzofuran-3,1'-cyclopropane]-4-yl)oxypyrimidin-5-yl]imidazolidine-2,4-dione;
3-[2-(3,3-dimethylisochroman-5-yl)oxypyrimidin-5-yl]-5,5-dimethyl-imidazolidine-2,4-dione;
5,5-dimethyl-3-[2-(7-methylspiro[1H-isobenzofuran-3,1'-cyclobutane]-4-yl)oxypyrimidin-5-yl]imidazolidine-2,4-dione;
(5R)-5-ethyl-3-[2-(7-methylspiro[2H-benzofuran-3,1'-cyclopropane]-4-yl)oxypyrimidin-5-yl]imidazolidine-2,4-dione;
(5R)-5-ethyl-3-[6-(7-methylspiro[2H-benzofuran-3,1'-cyclopropane]-4-yl)oxy-3-pyridyl]imidazolidine-2,4-dione;
(5R)-5-ethyl-3-{6-[(3,3,7-trimethyl-2,3-dihydro-1-benzofuran-4-yl)oxy]-3-pyridinyl}-2,4-imidazolidinedione;
(5R)-5-ethyl-3-{2-[(3,3,7-trimethyl-2,3-dihydro-1-benzofuran-4-yl)oxy]-5-pyrimidinyl}-2,4-imidazolidinedione;
(5R)-5-ethyl-5-methyl-3-[6-(7-methylspiro[2H-benzofuran-3,1'-cyclopropane]-4-yl)oxy-3-pyridyl]imidazolidine-2,4-dione;
(5R)-3-[6-(3,3-dimethylisochroman-5-yl)oxy-3-pyridyl]-5-ethyl-5-methyl-imidazolidine-2,4-dione;
(5R)-3-[6-[(3,3-diethyl-1H-isobenzofuran-4-yl)oxy]-3-pyridyl]-5-ethyl-5-methyl-imidazolidine-2,4-dione;
(5R)-5-ethyl-5-methyl-3-[6-[(2,4,4-trimethyl-3,1-benzoxazin-5-yl)oxy]-3-pyridyl]imidazolidine-2,4-dione;
(5R)-3-{6-[(3,3-dimethyl-1,3-dihydro-2-benzofuran-4-yl)oxy]-3-pyridinyl}-5-ethyl-5-methyl-2,4-imidazolidinedione;
5,5-dimethyl-3-[6-(7-methylspiro[2H-benzofuran-3,1'-cyclopropane]-4-yl)oxy-3-pyridyl]imidazolidine-2,4-dione;
or a pharmaceutically acceptable salt and/or solvate thereof and/or derivative thereof.

When W is group (Wa), suitably the compound of formula (I) is selected from:
3-[2-[(3,3-dimethyl-1H-isobenzofuran-5-yl)oxy]pyrimidin-5-yl]-5,5-dimethyl-imidazolidine-2,4-dione;
3-[2-[(3,3-diethyl-1H-isobenzofuran-5-yl)oxy]pyrimidin-5-yl]-5,5-dimethyl-imidazolidine-2,4-dione;
3-[2-[(3-tert-butyl-1,3-dihydroisobenzofuran-5-yl)oxy]pyrimidin-5-yl]-5,5-dimethyl-imidazolidine-2,4-dione (enantiomer 1);
3-[2-[(3-tert-butyl-1,3-dihydroisobenzofuran-5-yl)oxy]pyrimidin-5-yl]-5,5-dimethyl-imidazolidine-2,4-dione (enantiomer 2);
5,5-dimethyl-3-[2-[[3-methyl-3-(trifluoromethyl)-1H-isobenzofuran-5-yl]oxy]pyrimidin-5-yl]imidazolidine-2,4-dione (enantiomer 1);
5,5-dimethyl-3-[2-[[3-methyl-3-(trifluoromethyl)-1H-isobenzofuran-5-yl]oxy]pyrimidin-5-yl]imidazolidine-2,4-dione (enantiomer 2);
3-[2-[(3-ethyl-1,3-dihydroisobenzofuran-5-yl)oxy]pyrimidin-5-yl]-5,5-dimethyl-imidazolidine-2,4-dione (enantiomer 1);
3-[2-[(3-ethyl-1,3-dihydroisobenzofuran-5-yl)oxy]pyrimidin-5-yl]-5,5-dimethyl-imidazolidine-2,4-dione (enantiomer 2);
3-[2-[(3-cyclopropyl-1,3-dihydroisobenzofuran-5-yl)oxy]pyrimidin-5-yl]-5,5-dimethyl-imidazolidine-2,4-dione (enantiomer 1);
3-[2-[(3-cyclopropyl-1,3-dihydroisobenzofuran-5-yl)oxy]pyrimidin-5-yl]-5,5-dimethyl-imidazolidine-2,4-dione (enantiomer 2);
5,5-dimethyl-3-(2-spiro[1H-isobenzofuran-3,1'-cyclobutane]-5-yloxypyrimidin-5-yl)imidazolidine-2,4-dione;
5,5-dimethyl-3-(2-spiro[1H-isobenzofuran-3,1'-cyclopentane]-5-yloxypyrimidin-5-yl)imidazolidine-2,4-dione;
5,5-dimethyl-3-[2-[[3-(trifluoromethyl)-1,3-dihydroisobenzofuran-5-yl]oxy]pyrimidin-5-yl]imidazolidine-2,4-dione (enantiomer 1);
5,5-dimethyl-3-[2-[[3-(trifluoromethyl)-1,3-dihydroisobenzofuran-5-yl]oxy]pyrimidin-5-yl]imidazolidine-2,4-dione (enantiomer 2);
3-[2-[(3,3-dimethyl-2H-benzofuran-5-yl)oxy]pyrimidin-5-yl]-5,5-dimethyl-imidazolidine-2,4-dione;
3-[2-(4,4-dimethylisochroman-6-yl)oxypyrimidin-5-yl]-5,5-dimethyl-imidazolidine-2,4-dione;
(5R)-3-[2-[(3,3-dimethyl-1H-isobenzofuran-5-yl)oxy]pyrimidin-5-yl]-5-ethyl-5-methyl-imidazolidine-2,4-dione;
(5R)-3-[2-[(3,3-diethyl-1H-isobenzofuran-5-yl)oxy]pyrimidin-5-yl]-5-ethyl-5-methyl-imidazolidine-2,4-dione;
(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 1);
(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 2);
(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 1);
(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 2);
(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 1);
(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 2);
(5R)-5-ethyl-5-methyl-3-(2-spiro[1H-isobenzofuran-3,1'-cyclobutane]-5-yloxypyrimidin-5-yl)imidazolidine-2,4-dione;
(5R)-5-ethyl-5-methyl-3-(2-spiro[1H-isobenzofuran-3,1'-cyclopentane]-5-yloxypyrimidin-5-yl)imidazolidine-2,4-dione;
(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 1);
(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 2);
(5R)-3-[2-[(3,3-dimethyl-2H-benzofuran-5-yl)oxy]pyrimidin-5-yl]-5-ethyl-5-methyl-imidazolidine-2,4-dione;
(5R)-3-[2-(4,4-dimethylisochroman-6-yl)oxypyrimidin-5-yl]-5-ethyl-5-methyl-imidazolidine-2,4-dione;
(5R)-3-[6-[(3,3-dimethyl-1H-isobenzofuran-5-yl)oxy]-3-pyridyl]-5-ethyl-5-methyl-imidazolidine-2,4-dione;
(5R)-3-[6-[(3,3-diethyl-1H-isobenzofuran-5-yl)oxy]-3-pyridyl]-5-ethyl-5-methyl-imidazolidine-2,4-dione;
(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 1);

(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 2);
(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-[6-[(3-ethyl-1,3-dihydroisobenzofuran-5-yl)oxy]-3-pyridyl]-5-methyl-imidazolidine-2,4-dione (diastereoisomer 1);
(5R)-5-ethyl-3-[6-[(3-ethyl-1,3-dihydroisobenzofuran-5-yl)oxy]-3-pyridyl]-5-methyl-imidazolidine-2,4-dione (diastereoisomer 2);
(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 1);
(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 2);
(5R)-5-ethyl-5-methyl-3-(6-spiro[1H-isobenzofuran-3,1'-cyclobutane]-5-yloxy-3-pyridyl)imidazolidine-2,4-dione;
(5R)-5-ethyl-5-methyl-3-(6-spiro[1H-isobenzofuran-3,1'-cyclopentane]-5-yloxy-3-pyridyl)imidazolidine-2,4-dione;
(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 1);
(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 2);
(5R)-3-[6-[(3,3-dimethyl-2H-benzofuran-5-yl)oxy]-3-pyridyl]-5-ethyl-5-methyl-imidazolidine-2,4-dione;
(5R)-3-[6-(4,4-dimethylisochroman-6-yl)oxy-3-pyridyl]-5-ethyl-5-methyl-imidazolidine-2,4-dione;
3-[6-[(3,3-diethyl-1H-isobenzofuran-5-yl)oxy]-3-pyridyl]-5,5-dimethyl-imidazolidine-2,4-dione;
3-[6-[(3-tert-butyl-1,3-dihydroisobenzofuran-5-yl)oxy]-3-pyridyl]-5,5-dimethyl-imidazolidine-2,4-dione (enantiomer 1);
3-[6-[(3-tert-butyl-1,3-dihydroisobenzofuran-5-yl)oxy]-3-pyridyl]-5,5-dimethyl-imidazolidine-2,4-dione (enantiomer 2);
5,5-dimethyl-3-[6-[[3-methyl-3-(trifluoromethyl)-1H-isobenzofuran-5-yl]oxy]-3-pyridyl]imidazolidine-2,4-dione (enantiomer 1);
5,5-dimethyl-3-[6-[[3-methyl-3-(trifluoromethyl)-1H-isobenzofuran-5-yl]oxy]-3-pyridyl]imidazolidine-2,4-dione (enantiomer 2);
3-[6-[(3-ethyl-1,3-dihydroisobenzofuran-5-yl)oxy]-3-pyridyl]-5,5-dimethyl-imidazolidine-2,4-dione (enantiomer 1);
3-[6-[(3-ethyl-1,3-dihydroisobenzofuran-5-yl)oxy]-3-pyridyl]-5,5-dimethyl-imidazolidine-2,4-dione (enantiomer 2);
3-[6-[(3-cyclopropyl-1,3-dihydroisobenzofuran-5-yl)oxy]-3-pyridyl]-5,5-dimethyl-imidazolidine-2,4-dione (enantiomer 1);
3-[6-[(3-cyclopropyl-1,3-dihydroisobenzofuran-5-yl)oxy]-3-pyridyl]-5,5-dimethyl-imidazolidine-2,4-dione (enantiomer 2);
5,5-dimethyl-3-(6-spiro[1H-isobenzofuran-3,1'-cyclobutane]-5-yloxy-3-pyridyl)imidazolidine-2,4-dione;
5,5-dimethyl-3-(6-spiro[1H-isobenzofuran-3,1'-cyclopentane]-5-yloxy-3-pyridyl)imidazolidine-2,4-dione;
5,5-dimethyl-3-[6-[[3-(trifluoromethyl)-1,3-dihydroisobenzofuran-5-yl]oxy]-3-pyridyl]imidazolidine-2,4-dione (enantiomer 1);
5,5-dimethyl-3-[6-[[3-(trifluoromethyl)-1,3-dihydroisobenzofuran-5-yl]oxy]-3-pyridyl]imidazolidine-2,4-dione (enantiomer 2);
3-[6-[(3,3-dimethyl-2H-benzofuran-5-yl)oxy]-3-pyridyl]-5,5-dimethyl-imidazolidine-2,4-dione;
3-[6-(4,4-dimethylisochroman-6-yl)oxy-3-pyridyl]-5,5-dimethyl-imidazolidine-2,4-dione;
(5R)-3-[6-[(3,3-dimethyl-1H-isobenzofuran-5-yl)oxy]-5-methyl-3-pyridyl]-5-ethyl-5-methyl-imidazolidine-2,4-dione;
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 1);
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 2);
(5R)-5-ethyl-5-methyl-3-(5-methyl-6-spiro[1H-isobenzofuran-3,1'-cyclobutane]-5-yloxy-3-pyridyl)imidazolidine-2,4-dione;
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 1);
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 2);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 1);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 2);
(5R)-3-[6-[(3,3-dimethyl-1H-isobenzofuran-5-yl)oxy]-3-pyridyl]-5-ethyl-imidazolidine-2,4-dione;
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-(6-spiro[1H-isobenzofuran-3,1'-cyclobutane]-5-yloxy-3-pyridyl)imidazolidine-2,4-dione;
(5R)-3-[6-[(3,3-dimethyl-2H-benzofuran-5-yl)oxy]-3-pyridyl]-5-ethyl-imidazolidine-2,4-dione;
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-(2-spiro[1H-isobenzofuran-3,1'-cyclobutane]-5-yloxypyrimidin-5-yl)imidazolidine-2,4-dione;
(5R)-3-{4-[(3,3-dimethyl-1,3-dihydro-2-benzofuran-5-yl)oxy]phenyl}-5-ethyl-5-methyl-2,4-imidazolidinedione; and
(5R)-3-[4-(1,3-dihydro-2-benzofuran-5-yloxy)phenyl]-5-methyl-2,4-imidazolidinedione;
or a pharmaceutically acceptable salt and/or solvate thereof and/or derivative thereof.

Suitably, the compound of formula (I) contains a (Wa) group corresponding to one of the following phenol groups:

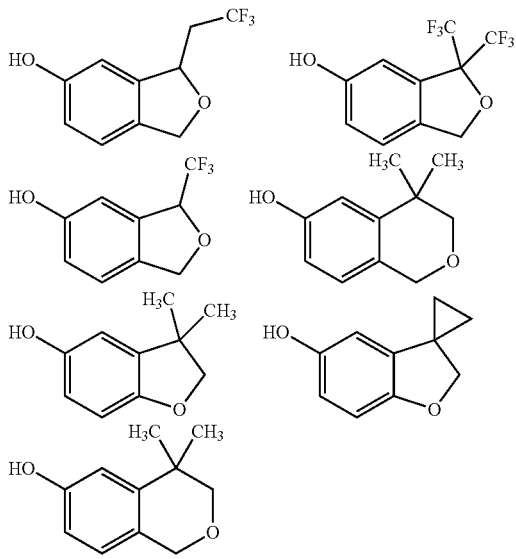

Suitably, the compound of formula (I) contains a (Wb) group corresponding to one of the following phenol groups:

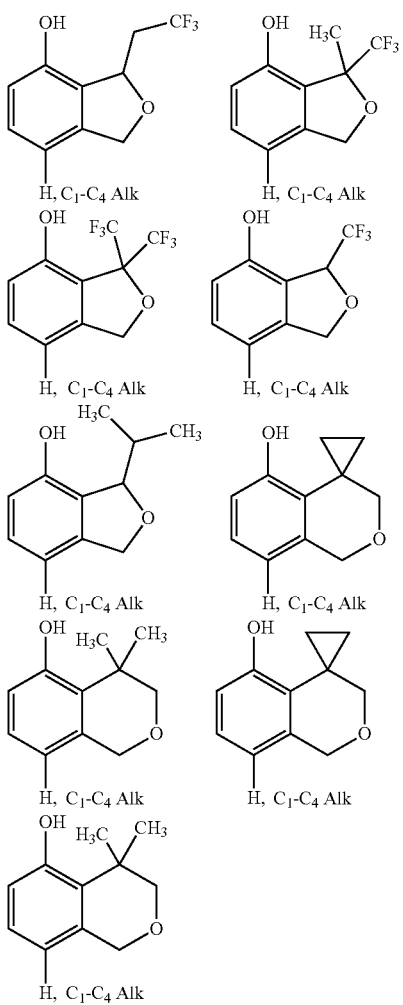

Alternatively, when the compound of formula (I) contains a (Wb) group corresponding to one of the following phenol groups:

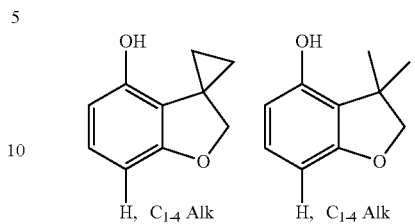

For the avoidance of doubt, the embodiments of any one feature of the compounds of formula (I) may be combined with any embodiment of another feature of compounds of formula (I) to create a further embodiment.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, n-butyl, isobutyl, sec-butyl, tert-butyl, cyclopropyl and cyclobutyl. A particular group of exemplary $C_{1-4}$alkyl groups are methyl, ethyl, n-propyl, isopropyl, n-butyl, isobutyl, sec-butyl, tert-butyl. An example of $C_{1-4}$alkoxy is methoxy.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary halo$C_{1-4}$ alkyl include methoxy and ethoxy groups substituted with one to three halo atoms, in particular one to three fluoro atoms.

The term '5 or 6 membered saturated or unsaturated heterocycle, with at least one O atom' includes for example dihydrofuran, dihydropyran, furan, pyran, oxazole, isoxazole, oxazine, dioxine, morpholine or 1,3-dioxalane.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) for use the prophylaxis of acute noise-induced hearing loss, for use in a method of preventing acute noise-induced hearing loss, and for use in the manufacture of a medicament for the prophylaxis of acute noise-induced hearing loss.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the hydantoin, for example with a group "L" as illustrated below:

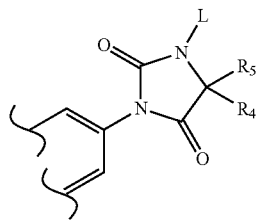

A compound of formula (I) may be functionalised via the secondary nitrogen of the hydantoin with a group L, wherein L is selected from:
a) —PO(OH)O$^-$.M$^+$, wherein M$^+$ is a pharmaceutically acceptable monovalent counterion,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^X$)—PO(OH)O$^-$.M$^+$, wherein R$^X$ is hydrogen or C$_{1-3}$ alkyl,
e) —CH(R$^X$)—PO(O$^-$)$_2$.2M$^+$,
f) —CH(R$^X$)—PO(O$^-$)$_2$.D$^{2+}$
g) —SO$_3^-$.M$^+$,
h) —CH(R$^X$)—SO$_3^-$.M$^+$, and
i) —CO—CH$_2$CH$_2$—CO$_2$.M$^+$.

All isomers of formula (I) and their pharmaceutically acceptable derivatives, including all geometric, tautomeric and optical forms, and mixtures thereof (e.g. racemic mixtures) are contemplated for the uses and method of the invention. Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

Isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment") are also contemplated for the uses and method of the invention. Examples of isotopes that can be incorporated into compounds of the invention include isotopes of hydrogen, carbon, nitrogen, oxygen, fluorine, iodine and chlorine such as $^2$H (deuterium), $^3$H, $^{11}$C, $^{13}$C, $^{14}$C, $^{18}$F, $^{123}$I or $^{125}$I, which may be naturally occurring or non-naturally occurring isotopes.

Compounds of formula (I) and pharmaceutically acceptable salts of said compounds that contain the aforementioned isotopes and/or other isotopes of other atoms are contemplated for use for the uses and method of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof.

Compounds of formula (I), and salts and solvates thereof wherein W is group (Wc) may be prepared by the general methods outlined in WO2011/069951.

Compounds of formula (I), and salts and solvates thereof wherein W is group (Wb) may be prepared by the general methods outlined in WO2012/076877.

Compounds of formula (I), and salts and solvates thereof wherein W is group (Wa) may be prepared by the general methods outlined in WO2012/168710 (application number PCT/GB2012/051278).

The compounds of formula (I) or their pharmaceutically acceptable salts and/or solvates and/or derivatives may be of use for the prophylaxis of acute noise-induced hearing loss via the modulation of Kv3.1 or Kv3.3 or Kv3.1 and Kv3.3 channels. As used herein, a modulator of Kv3.1 or Kv3.3 is a compound which positively alters the properties of the particular channel. Modulation of Kv3.1 and/or Kv3.2 channels in higher auditory circuits may be beneficial in preventing or reducing the onset of tinnitus resulting from noise-induced hearing loss. Compounds of formula (I) may be tested in the assay of Biological Example 1 to determine their modulatory properties.

In certain aspects of the prophylaxis of noise-induced hearing loss it may be of benefit to utilise a modulator of Kv3.3, Kv3.2 or Kv3.1 which demonstrates a particular selectivity profile between the three channels. For example a compound may be selective for modulation of Kv3.3 channels over modulation of Kv3.1 channels demonstrating, for example, at least a 2 fold, 5 fold or 10 fold activity for Kv3.3 channels than for Kv3.1 channels. For example a compound may be selective for modulation of Kv3.1 channels over modulation of Kv3.3 channels demonstrating, for example, at least a 2 fold, 5 fold or 10 fold activity for Kv3.1 channels than for Kv3.3 channels. Alternatively, a compound may be selective for modulation of Kv3.3 channels over modulation of Kv3.2 channels demonstrating, for example, at least a 2 fold, 5 fold or 10 fold activity for Kv3.3 channels than for Kv3.2 channels. Alternatively, a compound may be selective for modulation of Kv3.2 channels over modulation of Kv3.3 channels demonstrating, for example, at least a 2 fold, 5 fold or 10 fold activity for Kv3.2 channels than for Kv3.3 channels. As a further alternative, a compound may be selective for modulation of Kv3.1 channels over modulation of Kv3.2 channels demonstrating, for example, at least a 2 fold, 5 fold or 10 fold activity for Kv3.1 channels than for Kv3.2 channels. As a further alternative, a compound may be selective for modulation of Kv3.2 channels over modulation of Kv3.1 channels demonstrating, for example, at least a 2 fold, 5 fold or 10 fold activity for Kv3.2 channels than for Kv3.1 channels. In other cases a compound may demonstrate comparable activity between modulation of Kv3.3 and Kv3.1 channels, for example the activity for each channel is less than 2 fold that for the other channel, such as less than 1.5 fold or less than 1.2 fold. In other cases a compound may demonstrate comparable activity between modulation of Kv3.3 and Kv3.2 channels, for example the activity for each channel is less than 2 fold that for the other channel, such as less than 1.5 fold or less than 1.2 fold. In another case a compound may demonstrate comparable activity between modulation of Kv3.1 and Kv3.2 channels, for example the activity for each channel is less than 2 fold that for the other channel, such as less than 1.5 fold or less than 1.2 fold. In other cases a compound may demonstrate comparable activity between modulation of Kv3.3, Kv3.2 and Kv3.1 channels, for example the activity for each channel is less than 2 fold that for any other channel, such as less than 1.5 fold or less than 1.2 fold. The activity of a compound is suitably quantified by its potency as indicated by an $EC_{50}$ value.

The compounds of formula (I) or their pharmaceutically acceptable salts and/or solvates may be of use for the prophylaxis of acute noise-induced hearing loss via the modulation of Kv3.1 or Kv3.3 or Kv3.1 and Kv3.3 channels. The compounds of formula (I), or their pharmaceutically acceptable salts and/or solvates, may be used in the form of a derivative thereof.

The term "prophylaxis" is used herein to mean preventing symptoms of a disease or disorder in a subject or preventing recurrence of symptoms of a disease or disorder in an afflicted subject and is not limited to complete prevention of an affliction. The term "prophylaxis of acute noise-induced hearing loss" is therefore used herein to mean the prevention of symptoms of acute noise-induced hearing loss becoming established in a subject who may be (i.e. is at risk of being or is expected to be) or has recently been exposed to noise which could result in acute hearing loss. "Prophylaxis of acute noise-induced hearing loss" does not require the complete prevention of the symptoms of acute noise-induced hearing loss i.e. a reduction, mitigation or modulation in the severity of the acute noise-induced hearing loss is also encompassed.

The invention also provides a method of preventing acute noise-induced hearing loss, which comprises administering to a subject in need thereof an effective amount of a compound of formula (I) or a pharmaceutically acceptable salt and/or solvate thereof. The compounds of formula (I), or their pharmaceutically acceptable salts and/or solvates, may be used in the form of a derivative thereof.

The invention also provides a compound of formula (I), or a pharmaceutically acceptable salt and/or solvate thereof, for use in the prophylaxis of acute noise-induced hearing loss. The compounds of formula (I), or their pharmaceutically acceptable salts and/or solvates, may be used in the form of a derivative thereof.

The invention also provides the use of a compound of formula (I), or a pharmaceutically acceptable salt and/or solvate thereof, in the manufacture of a medicament for the prophylaxis of acute noise-induced hearing loss. The compounds of formula (I), or their pharmaceutically acceptable salts and/or solvates, may be used in the form of a derivative thereof.

"Acute hearing loss" is defined as hearing loss which occurs rapidly over a period of hours or days. For example, hearing loss may occur over a period of minutes, hours or days (for example over a period of up to 1 day, such as up to 2 days, 3 days, 4 days, 5 days, 6 days or 7 days). Acute hearing loss will typically be caused by exposure to loud sound or blast. Hearing loss caused by exposure to loud sound or blast is referred to herein as "noise-induced induced hearing loss". "Acute noise-induced hearing loss" is therefore hearing loss which occurs rapidly over a period of hours or days caused by exposure to loud sound or blast.

Important symptoms of acute hearing loss include:
1. a shift in the auditory threshold, i.e. an increase in the minimum sound level of a pure tone that can be heard with no other sound present;
2. tinnitus; and
3. degradation in central auditory processing, for example auditory temporal processing and/or speech understanding.

For use in therapy the compounds of formula (I) are usually administered as a pharmaceutical composition. Also provided is a pharmaceutical composition comprising a compound of formula (I), or a pharmaceutically acceptable salt and/or solvate thereof, and a pharmaceutically acceptable carrier. The compounds of formula (I), or their pharmaceutically acceptable salts and/or solvates, may be used in the form of a derivative thereof.

The compounds of formula (I) or their pharmaceutically acceptable salts and/or solvates thereof may be administered by any convenient method, e.g. by oral, parenteral, buccal, sublingual, nasal, rectal or transdermal administration, and the pharmaceutical compositions adapted accordingly. The compounds of formula (I), or their pharmaceutically acceptable salts and/or solvates, may be used in the form of a derivative thereof. Other possible routes of administration include intratympanic and intracochlear. Suitably, the compound of formula (I) or its pharmaceutically acceptable salt and/or solvate and/or derivative thereof is administered orally.

The compounds of formula (I) or their pharmaceutically acceptable salts and/or solvates thereof which are active when given orally can be formulated as liquids or solids, e.g. as syrups, suspensions, emulsions, tablets, capsules or lozenges. The compounds of formula (I), or their pharmaceutically acceptable salts and/or solvates, may be used in the form of a derivative thereof.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

As described above, acute noise-induced hearing loss may be caused by events such as exposure to loud noise or a blast.

A "loud" noise or blast may be at least 90 dB, for example, at least 100 dB, at least 110 dB, at least 120 dB or at least 130 dB. However, it will be appreciated that the frequency and duration of the noise or blast will also determine whether or not acute noise-induced hearing loss could be anticipated to occur. For example, a noise or blast of lower intensity may still result in acute hearing loss if of sufficient duration. Furthermore, different individuals will have different sensitivity to noise exposure.

In these cases, where it is anticipated that a future event may result in acute noise-induced hearing loss, the compound of formula (I) or a pharmaceutically acceptable salt, solvate and/or derivative thereof may be administered before the event in order to prevent or reduce acute noise-induced hearing loss. The administration of compound (I) or a pharmaceutically acceptable salt, solvate and/or derivative thereof may prevent any acute noise-induced hearing loss, or may reduce the severity of the acute noise-induced hearing loss or may mitigate other symptoms arising from acute noise-induced hearing loss, such as tinnitus.

In one embodiment, administration of the compound of formula (I) or a pharmaceutically acceptable salt, solvate and/or derivative thereof is initiated before an event which is anticipated to cause acute noise-induced hearing loss.

Thus, in one embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanent tinnitus.

The invention provides a method for preventing or reducing the development of permanent tinnitus due to exposure to a noise or blast which is anticipated to cause acute noise-induced hearing loss, the method comprising administering a compound of formula (I) or a pharmaceutically acceptable salt, solvate and/or derivative thereof to a subject in advance of exposure of the subject to a noise or blast which is anticipated to cause acute noise-induced hearing loss.

In another embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of a permanent shift in auditory thresholds.

The invention provides a method for preventing or reducing the development of a permanent shift in auditory thresholds due to exposure to a noise or blast which is anticipated to cause acute noise-induced hearing loss, the method comprising administering a compound of formula (I) or a pharmaceutically acceptable salt, solvate and/or derivative thereof to a subject in advance of exposure of the subject to a noise or blast which is anticipated to cause acute noise-induced hearing loss.

In a further embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanently degraded central auditory processing, including for example auditory temporal processing and/or speech understanding.

The invention provides a method for preventing or reducing the development of permanently degraded central auditory processing (including for example auditory temporal processing and/or speech understanding) due to exposure to a noise or blast which is anticipated to cause acute noise-induced hearing loss, the method comprising administering a compound of formula (I) or a pharmaceutically acceptable salt, solvate and/or derivative thereof to a subject in advance of exposure of the subject to a noise or blast which is anticipated to cause acute noise-induced hearing loss.

For example, administration of the compound of formula (I) or a pharmaceutically acceptable salt, solvate and/or derivative thereof may be initiated up to 2 weeks in advance, such as up to 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes in advance of an event which is anticipated to cause acute noise-induced hearing loss. The compound of formula (I) or a pharmaceutically acceptable salt, solvate and/or derivative thereof may be administered on multiple occasions before an event which is anticipated to cause acute noise-induced hearing loss.

It will be appreciated that administration in advance may be in circumstances where the subject is considered to be at risk of exposure to a noise or blast which is anticipated to cause acute noise-induced hearing loss and is not limited to those circumstances where such exposure ultimately occurs.

Alternatively, administration of the compound of formula (I) or a pharmaceutically acceptable salt, solvate and/or derivative thereof may be initiated during an event which is anticipated to result in acute noise-induced hearing loss.

In one embodiment, administration of the compound of formula (I) or a pharmaceutically acceptable salt, solvate and/or derivative thereof is initiated during an event which is anticipated to cause acute noise-induced hearing loss. The compound of formula (I) or a pharmaceutically acceptable salt, solvate and/or derivative thereof may be administered on multiple occasions during an event which is anticipated to cause acute noise-induced hearing loss.

Thus, in one embodiment, a compound of formula (I) or a pharmaceutically acceptable salt, solvate and/or derivative thereof is initially administered during a noise or blast which is anticipated to cause acute noise-induced hearing loss, for preventing or reducing the development of permanent tinnitus.

The invention provides a method for preventing or reducing the development of permanent tinnitus due to exposure to a noise or blast which is anticipated to cause acute noise-induced hearing loss, the method comprising initially administering a compound of formula (I) or a pharmaceutically acceptable salt, solvate and/or derivative thereof to a subject during exposure of the subject to a noise or blast which is anticipated to cause acute noise-induced hearing loss.

In another embodiment, a compound of formula (I) or a pharmaceutically acceptable salt, solvate and/or derivative thereof is initially administered during a noise or blast which is anticipated to cause acute noise-induced hearing loss, for preventing or reducing the development of a permanent shift in the auditory threshold.

The invention provides a method for preventing or reducing the development of a permanent shift in the auditory threshold due to exposure to a noise or blast which is anticipated to cause acute noise-induced hearing loss, the method comprising initially administering a compound of formula (I) or a pharmaceutically acceptable salt, solvate and/or derivative thereof to a subject during exposure of the subject to a noise or blast which is anticipated to cause acute noise-induced hearing loss.

In a further embodiment, a compound of formula (I) or a pharmaceutically acceptable salt, solvate and/or derivative thereof is initially administered during a noise or blast which is anticipated to cause acute noise-induced hearing loss, for preventing or reducing the development of permanently degraded central auditory processing, including auditory temporal processing and/or speech understanding.

The invention provides a method for preventing or reducing the development of permanently degraded central auditory processing (including auditory temporal processing and/or speech understanding) due to exposure to a noise or blast which is anticipated to cause acute noise-induced hearing loss, the method comprising initially administering a compound of formula (I) or a pharmaceutically acceptable salt, solvate and/or derivative thereof to a subject during exposure of the subject to a noise or blast which is anticipated to cause acute noise-induced hearing loss.

Alternatively, administration of the compound of formula (I) or a pharmaceutically acceptable salt, solvate and/or derivative thereof may be initiated after an event which is anticipated to result in acute noise-induced hearing loss.

In one embodiment, administration of the compound of formula (I) or a pharmaceutically acceptable salt, solvate and/or derivative thereof is initiated after an event which is anticipated to cause acute noise-induced hearing loss.

Thus, in one embodiment, a compound of formula (I) or a pharmaceutically acceptable salt, solvate and/or derivative thereof is initially administered after a noise or blast which is anticipated to cause acute noise-induced hearing loss, for preventing or reducing the development of permanent tinnitus.

The invention provides a method for preventing or reducing the development of permanent tinnitus due to exposure to a noise or blast which is anticipated to cause acute noise-induced hearing loss, the method comprising initially administering a compound of formula (I) or a pharmaceutically acceptable salt, solvate and/or derivative thereof to a subject after exposure of the subject to a noise or blast which is anticipated to cause acute noise-induced hearing loss.

In another embodiment, a compound of formula (I) or a pharmaceutically acceptable salt, solvate and/or derivative thereof is initially administered after a noise or blast which is anticipated to cause acute noise-induced hearing loss, for preventing or reducing the development of a permanent shift in the auditory threshold.

The invention provides a method for preventing or reducing the development of a permanent shift in the auditory threshold due to exposure to a noise or blast which is anticipated to cause acute noise-induced hearing loss, the method comprising initially administering a compound of formula (I) or a pharmaceutically acceptable salt, solvate and/or derivative thereof to a subject after exposure of the subject to a noise or blast which is anticipated to cause acute noise-induced hearing loss.

In a further embodiment, a compound of formula (I) or a pharmaceutically acceptable salt, solvate and/or derivative thereof is initially administered after a noise or blast which is anticipated to cause acute noise-induced hearing loss, for preventing or reducing the development of permanently degraded central auditory processing, including for example auditory temporal processing and/or speech understanding.

The invention provides a method for preventing or reducing the development of permanently degraded central auditory processing (including for example auditory temporal processing and/or speech understanding) due to exposure to a noise or blast which is anticipated to cause acute noise-induced hearing loss, the method comprising initially administering a compound of formula (I) or a pharmaceutically acceptable salt, solvate and/or derivative thereof to a subject after exposure of the subject to a noise or blast which is anticipated to cause acute noise-induced hearing loss.

When the compound of formula (I) is administered after an event which is anticipated to cause acute noise-induced hearing loss in order to prevent or reduce the development of tinnitus and/or the development of a permanent shift in the auditory threshold and/or the development of permanently degraded central auditory processing (including for example auditory temporal processing and/or speech understanding), such administration is normally undertaken during the "acute phase" i.e. before the hearing loss has become established.

For example, administration of the compound of formula (I) or a pharmaceutically acceptable salt, solvate and/or derivative thereof may be initiated up to 2 weeks after an event, such as up to 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after an event which is anticipated to cause acute noise-induced hearing loss. In respect of methods intended to prevent or reduce the onset of tinnitus resulting from noise-induced hearing loss administration of the compound of formula (I) or a pharmaceutically acceptable salt, solvate and/or derivative thereof may be initiated up to 6 months after an event, such as up to 2 months, 1 month, 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after an event which is anticipated to cause acute noise-induced hearing loss. The compound of formula (I) or a pharmaceutically acceptable salt, solvate and/or derivative thereof may be administered on multiple occasions after an event which is anticipated to cause acute noise-induced hearing loss.

Administration of the compound of formula (I) or a pharmaceutically acceptable salt, solvate and/or derivative thereof will be continued for as long as required to achieve the benefit of the invention. Typically, administration will be for a period of at least 1 week, such as at least 2 weeks, 1 month, 2 months, 6 months, 1 year or indefinitely.

The compound of formula (I) or a pharmaceutically acceptable salt, solvate and/or derivative thereof may be administered for a period of up to 7 days (for example, up to 1 day, up to 2 days, up to 3 days, up to 4 days, up to 5 days, up to 6 days or up to 7 days), for 1-2 weeks (for example, 7-8 days, 7-9 days, 7-10 days, 7-11 days, 7-12 days, 7-13 days or 7-14 days), for 2-4 weeks (for example, 2-3 weeks or 2-4 weeks) or for 1-2 months (for example, 4-6 weeks or 4-8 weeks).

The compound of formula (I) or a pharmaceutically acceptable salt, solvate and/or derivative thereof may initially be administered up to 1 day in advance, such as up to 2 days in advance, up to 3 days in advance, up to 5 days in advance, up to 1 week in advance, up to 2 weeks in advance or up to 1 month in advance of a noise or blast which is anticipated to cause acute noise-induced hearing loss, administration which is initiated at any point in advance exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

Administration which is initiated during exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

The compound of formula (I) or a pharmaceutically acceptable salt, solvate and/or derivative thereof may be initiated up to 2 weeks after an event, such as up to 1 week, 6 days, 5 days, 4 days, 3 days, 2 days, 24 hours, 12 hours, 6 hours, 5 hours, 4 hours, 3 hours, 2 hours, 1 hour, 30 minutes or up to 15 minutes after the noise or blast which is anticipated to cause acute noise-induced hearing loss, administration which is initiated after exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

The ability of a compound of formula (I) or a pharmaceutically acceptable salt, solvate and/or derivative thereof to prevent permanent acute noise induced hearing loss may be quantified at a reasonable time period after the exposure to the noise or blast which is anticipated to cause acute noise-induced hearing loss using appropriate testing methodologies known to the skilled person. For example, it is suitably quantified 2 weeks to 2 months after the exposure to the noise or blast which is anticipated to cause acute noise-induced hearing loss, for example about 4 weeks after the exposure to the noise or blast which is anticipated to cause acute noise-induced hearing loss.

Suitably, quantifying permanent acute noise induced hearing loss is undertaken at least one week after administration of the a compound of formula (I) or a pharmaceutically acceptable salt, solvate and/or derivative thereof has been ceased, such as at least two weeks after, for example 2-4 weeks after, or at least one month after, for example one to two months after.

The ability of a compound of formula (I) or a pharmaceutically acceptable salt, solvate and/or derivative thereof to reduce the development of a of a permanent shift in the auditory threshold is suitably quantified by methods similar to those provided in Biological Example 2, such as measurement of hearing thresholds for pure tones at one or more frequencies between 500 Hz and 12 kHz.

Thus, in one embodiment is provided a compound of formula (I) or a pharmaceutically acceptable salt, solvate and/or derivative thereof for use in preventing or reducing the development of a permanent shift in the auditory threshold, wherein the permanent shift in auditory threshold is reduced by at least 10 dB, such as at least 15 dB, at least 20 dB, at least 30 dB, at least 40 dB, or completely.

The ability of a compound of formula (I) or a pharmaceutically acceptable salt, solvate and/or derivative thereof to reduce the development of permanent tinnitus is suitably quantified using, for example, the Tinnitus Handicap Inventory (Arch Otolaryngol Head Neck Surg. 1996 February; 122(2):143-8 and Development of the Tinnitus Handicap Inventory; Newman C W, Jacobson G P, Spitzer J B) and/or the Tinnitus Functional Index (Meikle et al. Ear Hear. 2012 March-April; 33(2):153-76. doi: 10.1097/AUD.0b013e31822f67c0) and/or assessment of minimum masking level (e.g. Jastreboff et al. Hear Res. 1994 November; 80(2):216-32).

Thus, in one embodiment is provided a compound of formula (I) or a pharmaceutically acceptable salt, solvate and/or derivative thereof for use in preventing or reducing the development of permanent tinnitus, wherein the permanent tinnitus is reduced by at least 10 points on the Tinnitus Handicap Inventory, and/or at least 10 points on the Tinnitus Functional Index, and/or at least 5 dB in minimum masking level. One method for evaluating whether tinnitus is experienced as a symptom of acute noise-induced hearing loss is described in the Experimental section under "Model 2".

The ability of a compound of formula (I) or a pharmaceutically acceptable salt, solvate and/or derivative thereof to reduce the development of permanently degraded central auditory processing is suitably quantified using a speech-in-noise test such as the Hearing In Noise Test (Nilsson et al., J Acoust Soc Am. 1994 February; 95(2):1085-99). An alternative method to quantify the development of central auditory processing deficits is described in the Experimental section under "Model 1".

Thus, in one embodiment is provided a compound of formula (I) or a pharmaceutically acceptable salt, solvate and/or derivative thereof for use in preventing or reducing the development of permanently degraded central auditory processing (including auditory temporal processing and/or speech understanding), wherein the permanently degraded central auditory processing as measured using the Hearing In Noise Test is reduced by at least 2 dB.

Also provided is a combination comprising a compound of formula (I) or a pharmaceutically acceptable salt, solvate and/or derivative thereof together with a further therapeutic agent or agents.

Also provided is a compound of formula (I), for use in combination with a further therapeutic agent or agents.

A compound of formula (I) or a pharmaceutically acceptable salt, solvate and/or derivative thereof may be administered in combination with another treatment for acute noise-induced hearing loss, for example an anti-inflammatory agent such as a steroidal anti-inflammatory agent such as dexamethasone. Thus, in one embodiment of the invention a compound of formula (I) or a pharmaceutically acceptable salt, solvate and/or derivative thereof is administered in combination with one or more anti-inflammatory agents, such as steroidal anti-inflammatory agents. In a further embodiment, the steroidal anti-inflammatory agent is dexamethasone.

When the compounds are used in combination with other therapeutic agents, the compounds may be administered separately, sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes. For example, the compound of formula (I) or a pharmaceutically acceptable salt, solvate and/or derivative thereof and the other therapeutic agent (such as a steroidal anti-inflammatory agent) may both be administered orally. Alternatively, the compound of formula (I) or a pharmaceutically acceptable salt, solvate and/or derivative thereof and the other therapeutic agent may be administered via an intratympanic or intracochlear route and the other therapeutic agent (such as a steroidal anti-inflammatory agent) may be administered orally.

When a compound of formula (I) or a pharmaceutically acceptable derivative thereof is used in combination with a second therapeutic agent active against noise-induced acute hearing loss the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Typically, the compound of formula (I) or a pharmaceutically acceptable salt, solvate and/or derivative thereof is administered to a human.

For use in therapy the a compound of formula (I) are usually administered as a pharmaceutical composition for example a composition comprising a compound of formula (I) or a pharmaceutically acceptable salt, solvate and/or derivative thereof, and a pharmaceutically acceptable carrier. Examples of such compositions, and methods of administration thereof, which compositions comprise a compound of formula (I), or a pharmaceutically acceptable salt, solvate and/or derivative thereof, are described hereinabove.

EXPERIMENTAL

Biological Example 1

The ability of the compounds to modulate the voltage-gated potassium channel subtypes Kv3.3/Kv3.2/3.1 may be determined using the following assay. Analogous methods may be used to investigate the ability of the compounds to modulate other channel subtypes.

Cell Biology

To assess compound effects on human Kv3.3 channels (hKv3.3), a stable cell line expressing human Kv3.3 channels was created by transfecting Chinese Hamster Ovary (CHO)-K1 cells with a pBacMire_KCNC-3 vector. Cells were cultured in DMEM/F12 (Gibco) supplemented with 10% Foetal Bovine Serum (Gibco), 1× non-essential amino acids (Invitrogen) and geneticin (G418) 400 microg/mL. Cells were grown and maintained at 37° C. in a humidified environment containing 5% $CO_2$ in air.

To assess compound effects on human Kv3.2 channels (hKv3.2), a stable cell line expressing human Kv3.2 channels (hKv3.2) was created by transfecting CHO-K1 cells with a pCIH5-hKv3.2 vector. Cells were cultured in DMEM/F12 medium supplemented by 10% Foetal Bovine Serum, 1× non-essential amino acids (Invitrogen) and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pcDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell Preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. For hKv3.2 and hKv3.1 assays, from the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. For hKv3.3 assays, from the holding potential of −70 mV, a first test pulse to 0 mV was applied for 500 ms and following a further 100 ms at −70 mV, a second pulse to 40 mV was applied for 200 ms. These longer test pulses were used to study inactivation of hKv3.3 channels. Test pulses protocol may be performed in the absence (pre-read) and presence (post-read) of the test compound. Pre- and post-reads may be separated by the compound addition followed by a 3 minute incubation.

Solutions and Drugs

The intracellular solution contained the following (in mM): K-gluconate 100, KCl 54, MgCl2 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): $CaCl_2$ 0.90, KCl 2.67, KH2PO4 1.47, MgCl.6H2O 0.493, NaCl 136.9, $Na_3PO_4$ 8.06, with a pH of 7.4.

Compounds of formula (I) (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the invention was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MO) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step were used to determine the positive modulation effect of each compound. Kv3 channel-mediated outward currents were measured determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (EC50) was determined by fitting of the concentration-response data using a four parameter logistic function in ActivityBase. For hKv3.3 assays, paired comparisons of evoked currents between pre- and post-drug additions were measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N'-phenylurea was obtained from ASINEX (Registry Number: 552311-06-5).

All of the Example compounds were tested in the above hKv3.1 and hKv3.2 assay measuring potentiation of Kv3.1 or Kv3.2 or Kv3.1 and Kv 3.2 (herein after "Kv3.1 and/or Kv3.2"). Kv3.1 and/or Kv3.2 positive modulators produce in the above assay an increase of whole-cell currents of, on average, at least 20% of the increase observed with 50 microM N-cyclohexyl-N-[(7,8-dimethyl-2-oxo-1,2-dihydro-3-quinolinyl)methyl]-N'-phenylurea. Thus, in the recombinant cell assays of Biological Example 1, all of the Example compounds act as positive modulators of Kv3.1 and/or Kv3.2.

The following compounds of formula (I) wherein W is group (Wc) were investigated as Kv3.3 channel modulators in the recombinant cell assay:

5,5-dimethyl-3-[2-({4-methyl-3-[(trifluoromethyl)oxy]phenyl}oxy)-5-pyrimidinyl]-2,4-imidazolidinedione (Example 57 of WO2011/069951);

(5R)-5-ethyl-5-methyl-3-[2-({4-methyl-3-[(trifluoromethyl)oxy]phenyl}oxy)-5-pyrimidinyl]-2,4-imidazolidinedione (Example 64 of WO2011/069951);

(5R)-5-ethyl-3-[2-({4-methyl-3-[(trifluoromethyl)oxy]phenyl}oxy)-5-pyrimidinyl]-2,4-imidazolidinedione (Example 79 of WO2011/069951).

The following compounds of formula (I) wherein W is group (Wb) were investigated as Kv3.3 channel modulators in the recombinant cell assay:

(5R)-5-ethyl-3-[6-(spiro[1-benzofuran-3,1'-cyclopropan]-4-yloxy)-3-pyridinyl]-2,4-imidazolidinedione (Example 15 of WO2012/076877);

5,5-dimethyl-3-[6-(spiro[1-benzofuran-3,1'-cyclopropan]-4-yloxy)-3-pyridinyl]-2,4-imidazolidinedione (Example 16 of WO2012/076877);

5,5-dimethyl-3-[2-(7-methylspiro[2H-benzofuran-3,1'-cyclopropane]-4-yl)oxypyrimidin-5-yl]imidazolidine-2,4-dione (Example 58 of WO2012/076877);

5,5-dimethyl-3-[6-(7-methylspiro[2H-benzofuran-3,1'-cyclopropane]-4-yl)oxy-3-pyridyl]imidazolidine-2,4-dione (Example 70 of WO2012/076877).

The following compounds of formula (I) wherein W is group (Wa) were investigated as Kv3.3 channel modulators in the recombinant cell assay:

5,5-dimethyl-3-[2-[[3-methyl-3-(trifluoromethyl)-1H-isobenzofuran-5-yl]oxy]pyrimidin-5-yl]imidazolidine-2,4-dione (enantiomer 1) (Example 5 of PCTGB2012/051278);

5,5-dimethyl-3-[2-[[3-methyl-3-(trifluoromethyl)-1H-isobenzofuran-5-yl]oxy]pyrimidin-5-yl]imidazolidine-2,4-dione (enantiomer 2) (Example 6 of PCTGB2012/051278);

(5R)-3-[6-[(3,3-dimethyl-1H-isobenzofuran-5-yl)oxy]-3-pyridyl]-5-ethyl-5-methyl-imidazolidine-2,4-dione (Example 33 of PCTGB2012/051278);

5,5-dimethyl-3-[6-[[3-methyl-3-(trifluoromethyl)-1H-isobenzofuran-5-yl]oxy]-3-pyridyl]imidazolidine-2,4-dione (enantiomer 1) (Example 52 of PCTGB2012/051278);

5,5-dimethyl-3-[6-[[3-methyl-3-(trifluoromethyl)-1H-isobenzofuran-5-yl]oxy]-3-pyridyl]imidazolidine-2,4-dione (enantiomer 2) (Example 53 of PCTGB2012/051278);

5,5-dimethyl-3-(6-spiro[1H-isobenzofuran-3,1'-cyclobutane]-5-yloxy-3-pyridyl)imidazolidine-2,4-dione (Example 58 of PCTGB2012/051278);

(5R)-3-[6-[(3,3-dimethyl-1H-isobenzofuran-5-yl)oxy]-5-methyl-3-pyridyl]-5-ethyl-5-methyl-imidazolidine-2,4-dione (Example 64 of PCTGB2012/051278);

(5R)-3-[6-[(3,3-dimethyl-1H-isobenzofuran-5-yl)oxy]-3-pyridyl]-5-ethyl-imidazolidine-2,4-dione (Example 72 of PCTGB2012/051278);

(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1) (Example 73 of PCTGB2012/051278);

(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2) (Example 74 of PCTGB2012/051278);

(5R)-5-ethyl-3-(6-spiro[1H-isobenzofuran-3,1'-cyclobutane]-5-yloxy-3-pyridyl)imidazolidine-2,4-dione (Example 75 of PCTGB2012/051278);

3-[6-[(3-tert-butyl-1,3-dihydroisobenzofuran-5-yl)oxy]-3-pyridyl]-5,5-dimethyl-imidazolidine-2,4-dione (enantiomer 1) (Example 50 of PCTGB2012/051278);

3-[6-[(3-tert-butyl-1,3-dihydroisobenzofuran-5-yl)oxy]-3-pyridyl]-5,5-dimethyl-imidazolidine-2,4-dione (Example 51 of PCTGB2012/051278).

A secondary analysis of the data from the hKv3.1, hKv3.2, and hKv3.3 assays described in Biological Example 1 may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1, Kv3.2 or Kv3.3 currents following the start of the −15 mV depolarising voltage pulse.

$$Y = (Y0 - Ymax) * \exp(-K*X) + Ymax$$

where:
Y0 is the current value at the start of the depolarising voltage pulse;
Ymax is the plateau current;
K is the rate constant, and $Tau_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1, Kv3.2, and Kv3.3 channels must activate and deactivate very rapidly in order to allow neurons to fire actions potentials at high frequency (Rudy and McBain, 2001, Trends in Neurosciences 24, 517-526).

Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2, and/or Kv3.3 channels will effectively behave as negative modulators of the channels, leading to a slowing of neuronal firing. This latter effect has been shown for certain of the compounds disclosed in WO2011/069951, where marked increases in $Tau_{act}$ can be observed from recordings made from "fast-firing" interneurons in the cortex of rat brain, using electrophysiological techniques, in vitro. The addition of the relevant compounds reduces the ability of the neurons to fire in response to trains of depolarising pulses at 300 Hz.

Therefore, although compounds of formula (I) may be identified act as positive modulators in the recombinant cell assay of Biological Example 1, those compounds which markedly increase the value of $Tau_{act}$ reduce the ability of neurons in native tissues to fire at high frequency.

Biological Example 2

Evaluation of the Efficacy of Modulators of Kv3 Channels in a Model of Acute Noise-Induced Hearing Loss in the Chinchilla The otoprotective efficacy (i.e. the ability to prevent or reduce the development of permanent acute noise-induced hearing loss) of an exemplary Kv3 modulator, Example 64 described within WO2011069951A1 ((5R)-5-ethyl-5- methyl-3-[2-({4-methyl-3-[(trifluoromethyl)oxy]phenyl}oxy)-5-pyrimidinyl]-2,4-imidazolidinedione), referred to herein as "COMPOUND X", was investigated using a chinchilla model of acute noise-induced hearing loss, as follows:

Materials and Methods

Subjects comprised male, 3 year old chinchillas (Laniger), 10 animals per group. Chinchillas were housed in the study facility for a minimum of 5 days prior to noise exposure. Food and water were available ad libitum. Animals were maintained at 21° C. on a 12/12 light/dark cycle.

Vehicle and Drug Preparation and Administration

Vehicle (20% Captisol®, 0.5% w/v HPMC K15M and 0.5% w/v Tween 80™) was prepared using autoclaved deionized water not more than one week prior to use. A suspension of COMPOUND X in the vehicle at 10 mg/ml was prepared less than 24 hours prior to administration. COMPOUND X was administered at 60 mg/kg via the intraperitoneal route, with doses 12 hours apart. Five injections were given pre-noise exposure and five post-noise exposure. On the day of noise exposure, injections were given 1.5 hours before the start of noise exposure and one hour after completion of the noise exposure protocol.

Noise Exposure

Animals were placed in a sound-attenuated booth for 15 minutes prior to noise exposure. Noise exposure consisted of a 105 dB SPL octave-band noise centered at 4 kHz (TDT GNS 40x white noise generator) for 6 hours duration. The noise was routed through an attenuator (TDT PA3), a filter (Krohn-Hite 3384) and a power amplifier (Sony 55ES) to a custom-built acoustic exponential horn with a maximum output at 4 kHz using an Altec 209E driver. The loudspeaker was suspended directly above the cage. During noise exposure, animals had access to water, but not food.

Auditory Brainstem Response

Auditory brainstem responses (ABRs) were collected prior to noise exposure and 21 days after noise exposure. All animals were anesthetized throughout the ABR procedure and prior to sacrifice with a 0.3 ml/kg IM injection of 50 mg/mL ketamine, 5 mg/mL xylazine, and 1 mg/kg acepromazine. Thresholds were measured in response to tone-bursts with 1 ms rise/fall and a 0 ms plateau gated by a Blackman envelope and centred at the frequencies of 2, 4, 6 and 8 kHz, presented at 30/s. Two intensity series were obtained for each animal from 100 to 0 dB peak SPL in 10 dB decrements with 512 sweeps per average. The recording epoch was 15 ms following stimulus onset. Responses were analogue filtered with a 30-3000 Hz band pass. Threshold is defined as the lowest intensity capable of eliciting a replicable, visually detectable auditory brainstem response in both intensity series.

Further details of these methods can also be found in Campbell et al. (2011) Hearing Research 282, 138-144.

Data Analysis

The thresholds for ABRs at the four different sound frequencies at day 21 post-noise exposure were compared to the thresholds at baseline, prior to noise exposure in order to determine a threshold shift for each animal. The data were then analysed using a 2-way ANOVA, with treatment and frequency as main factors.

Results

In this assay, COMPOUND X significantly reduced the permanent threshold shift in ABRs observed 21 days after noise exposure ($p<0.01$). Notably, this protection benefit is observed some time after administration of COMPOUND X has been ceased, indicating that the benefits are persistent. These results support the potential efficacy of COMPOUND X and of small molecule Kv3 channel modulators in general in the prevention or reduction of permanent acute noise-induced hearing loss.

Model 1—Evaluating Deficits in Central Auditory Processing

Research has shown that deficits in central auditory processing, in particular deficits in auditory temporal processing, contribute to the difficulties in understanding speech. A measure of auditory temporal processing that has been shown to correlate with the difficulty in understanding speech is gap detection (Mazelova et al. J. Exp Gerontol. 2003 January-February; 38(1-2):87-94).

Methods

The ability of an intervention to improve auditory temporal processing in a test animal may be examined using an auditory gap detection procedure.

Hearing thresholds are determined under anaesthesia using the auditory brainstem response (ABR) prior to the noise exposure. ABRs are recorded using subcutaneous needle electrodes in a sound attenuated chamber using pure tone bursts as stimuli (5 ms duration, frequency range 2-40 kHz).

The gap detection procedure evaluates the ability of the test animal to detect short gaps in background noise by measuring the degree of inhibition that the gap afforded in the animal's startle response to a subsequent loud sound, a phenomenon known as pre-pulse inhibition (PPI). Testing is performed in a sound attenuated chamber. During the testing procedure, the test animal is confined to a small wire mesh cage on a motion-sensitive platform. The animal's reflex movements are detected and transduced by a piezoelectric accelerometer. The startle response is evaluated in a 100 ms window beginning at the onset of the startle stimulus (a 110 dB SPL broad-band noise burst of 50 ms duration embedded in a background continuous broad-band noise of 65 dB SPL). Acoustic stimulation is presented via a loudspeaker placed 12 cm above the platform inside the chamber.

PPI of the startle response is induced by gaps of different durations (5-50 ms) preceding the startle stimulus by 70 ms. The degree of PPI is calculated from the startle response amplitude in the presence of the gap relative to the startle response amplitude in the absence of the gap. A two-way ANOVA with the Bonferroni post-hoc test is used to compare the degree of PPI before and after noise exposure and with or without the drug intervention.

A deficit in gap-induced PPI will indicate a degradation of temporal resolution. Thus, any compound that can reduce the deficit can potentially be effective in reducing central auditory processing deficits and thus may be beneficial in improving auditory temporal processing and speech understanding.

Model 2—Evaluating Whether Tinnitus is Experienced as a Symptom of Acute Noise-Induced Hearing Loss Chronic subjective tinnitus often emerges in human patients following noise trauma-induced hearing loss. A similar phenomenon is thought to occur in animals. Methods for determining whether animals are experiencing tinnitus following hearing loss have been developed (Turner, Prog Brain Res. 2007; 166:147-562007). A representative procedure is outlined below.

Methods

Following noise exposure, animals may be assessed for the presence of tinnitus using a gap pre-pulse inhibition of acoustic startle paradigm similar to that described by Turner et al. (Behav. Neurosci. 2006 February; 120(1):188-95). In this test animals were placed on a motion sensor that measured the startle amplitude of the animals in response to a sudden loud sound (115-dB SPL, 20-ms duration) emitted by a loudspeaker located in the ceiling of the cage. It is known that a brief, non-startling sound or "pre-pulse", prior to the startle sound can reduce the startle amplitude, a phenomenon known as pre-pulse inhibition. The pre-pulse may be substituted by a 50 ms silence gap in a constant sound 100 ms prior to the startle sound. If the gap is perceived by the animal, then startle response will be inhibited. However, if the animal has tinnitus, then the tinnitus sound may fill the gap and will the animal will startle as if there were no gap (reduced or absent gap pre-pulse inhibition). A drug that reduces the tinnitus will therefore restore gap pre-pulse inhibition.

The pitch of tinnitus is typically in the same range as the hearing loss, which in turn is most marked at the frequencies of the noise trauma. Thus each animal is typically tested for gap pre-pulse inhibition using gaps in tones of 10, 12.5, 16, 20, and 25 kHz at 60-65 dB SPL.

As a control, the animals may be tested with gaps in a broadband sound of the same amplitude. Irrespective of whether the animals have tinnitus, it is unlikely that the tinnitus would fill the gap in the broadband sound, and thus this provides a control for whether the noise-trauma might have affected the gap detection ability of the animals. Those noise-exposed animals demonstrating deficits in auditory gap pre-pulse inhibition are therefore expected to be suffering from tinnitus.

Hearing thresholds for clicks and tone bursts at 10, 16, 20, 24, and 32 kHz are estimated from auditory brainstem responses. Thresholds are obtained before and after noise trauma. Hearing thresholds for the noise exposed ear not significantly differing from those before noise-exposure (e.g. 10-20 dB SPL), will confirm that only mild hearing loss has occurred that would not interfere with the ability of the animals to perform the gap pre-pulse inhibition task.

An intervention which reduces tinnitus will restore gap pre-pulse inhibition in the animals that show evidence of tinnitus.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A method for preventing or reducing the development of a permanent shift in the auditory threshold due to noise exposure, by administering to a subject a compound of formula (I) or a pharmaceutically acceptable salt thereof, wherein the subject is at risk of being, or has recently been exposed to noise which could result in acute hearing loss:

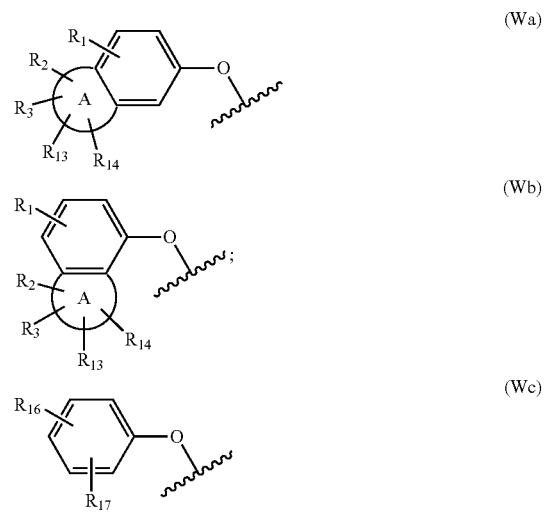

wherein:
W is group (Wa), group (Wb) or group (Wc):

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;
$R_{15}$ is H or $C_{1-4}$alkyl;
$R_{16}$ is halo, $C_{1-4}$ alkyl, $C_{1-4}$ alkoxy, halo-$C_{1-4}$alkyl, halo-$C_{1-4}$alkoxy, or CN;
$R_{17}$ is H, halo, cyano, $C_{1-4}$ alkyl or $C_{1-4}$ alkoxy; with the proviso that when $R_{17}$ is H, $R_{16}$ is not in the para position;
$R_4$ is $C_{1-4}$ alkyl;
$R_5$ is H or $C_{1-4}$ alkyl;
or $R_4$ and $R_5$ can be fused to form $C_{3-4}$ spiro carbocyclyl;
wherein $R_2$ and $R_3$ may be attached to the same or a different ring atom; $R_2$ may be attached to a fused ring atom; and wherein $R_{13}$ and $R_{14}$ may be attached to the same or a different ring atom.

2. The method of claim 1, wherein W is group (Wb).

3. The method according to claim 1, wherein administration of the compound of formula (I) is initiated before an event which could cause acute noise-induced hearing loss.

4. The method according to claim 3, wherein the compound of formula (I) is administered up to 2 weeks in advance of an event which could cause acute noise-induced hearing loss.

5. The method according to claim 1, wherein administration of the compound of formula (I) is initiated during an event which could cause acute noise-induced hearing loss.

6. The method according to claim 1, wherein administration of the compound of formula (I) is initiated after an event which could cause acute noise-induced hearing loss.

7. The method according to claim 6, wherein administration of the compound of formula (I) is initiated up to 2 weeks after an event which could cause acute noise-induced hearing loss.

8. The method according to claim 1, wherein administration of the compound of formula (I) or a pharmaceutically acceptable salt, thereof is for up to 7 days.

9. The method according to claim 1, wherein the compound of formula (I) is administered in combination with another therapeutic agent for the treatment or prophylaxis of acute noise-induced hearing loss.

10. The method of claim 1, wherein W is group (Wa).

11. The method of claim 1, wherein ring A is:

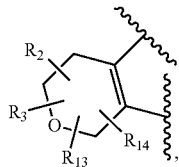
1

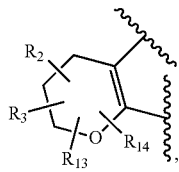
2

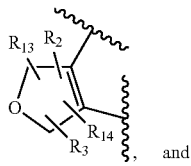
3

, and

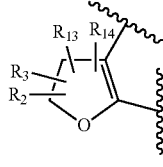
4 wherein

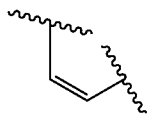

denotes a point at which ring A is fused to the phenyl ring.

12. The method of claim 1, wherein W is group (Wc).

13. The method according to claim 1, wherein Y is N.

14. The method according to claim 1, wherein Y is $CR_{15}$ and $R_{15}$ is H.

15. The method according to claim 1, wherein the compound of formula (I) is selected from the group consisting of:

(5R)-5-ethyl-5-methyl-3[2-({4-methyl-3-[(trifluoromethyl)oxy]phenyl}oxy)-5-pyrimidinyl]-2,4-imidazolidinedione;

(5R)-5-ethyl-3[2-({4-methyl-3-[(trifluoromethyl)oxy]phenyl}oxy)-5-pyrimidinyl]-2,4-imidazolidinedione;

5,5-dimethyl-3-[2-({4-methyl-3-[(trifluoromethyl)oxy]phenyl}oxy)-5-pyrimidinyl]-2,4-imidazolidinedione;

(5R)-5-ethyl-3-[6-(spiro[1-benzofuran-3,1'-cyclopropan]-4-yloxy)-3-pyridinyl]-2,4-imidazolidinedione;

5,5-dimethyl-3-[6-(spiro[1-benzofuran-3,1'-cyclopropan]-4-yloxy)-3-pyridinyl]-2,4-imidazolidinedione;

5,5-dimethyl-3-[2-(7-methylspiro[2H-benzofuran-3,1'-cyclopropane]-4-yl)oxypyrimidin-5-yl]imidazolidine-2,4-dione;

5,5-dimethyl-3-[6-(7-methylspiro[2H-benzofuran-3,1'-cyclopropane]-4-yl)oxy-3-pyridyl]imidazolidine-2,4-dione;

5,5-dimethyl-3-[2-[[3-methyl-3-(trifluoromethyl)-1H-isobenzofuran-5-yl]oxy]pyrimidin-5-yl]imidazolidine-2,4-dione (enantiomer 1);

5,5-dimethyl-3-[2-[[3-methyl-3-(trifluoromethyl)-1H-isobenzofuran-5-yl]oxy]pyrimidin-5-yl]imidazolidine-2,4-dione (enantiomer 2);

(5R)-3-[6-[(3,3-dimethyl-1H-isobenzofuran-5-yl)oxy]-3-pyridyl]-5-ethyl-5-methyl-imidazolidine-2,4-dione;

5,5-dimethyl-3-[6-[[3-methyl-3-(trifluoromethyl)-1H-isobenzofuran-5-yl]oxy]-3-pyridyl]imidazolidine-2,4-dione (enantiomer 1);

5,5-dimethyl-3-[6-[[3-methyl-3-(trifluoromethyl)-1H-isobenzofuran-5-yl]oxy]-3-pyridyl]imidazolidine-2,4-dione (enantiomer 2);

5,5-dimethyl-3-(6-spiro[1H-isobenzofuran-3,1'-cyclobutane]-5-yloxy-3-pyridyl)imidazolidine-2,4-dione;

(5R)-3-[6-[(3,3-dimethyl-1H-isobenzofuran-5-yl)oxy]-5-methyl-3-pyridyl]-5-ethyl-5-methyl-imidazolidine-2,4-dione;

(5R)-3-[6-[(3,3-dimethyl-1H-isobenzofuran-5-yl)oxy]-3-pyridyl]-5-ethyl-imidazolidine-2,4-dione;

(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1);

(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2);

(5R)-5-ethyl-3-(6-spiro[1H-isobenzofuran-3,1'-cyclobutane]-5-yloxy-3-pyridyl)imidazolidine-2,4-dione 3-[6-[(3-tert-butyl-1,3-dihydroisobenzofuran-5-yl)oxy]-3-pyridyl]-5,5-dimethyl-imidazolidine-2,4-dione (enantiomer 1); and 3-[6-[(3-tert-butyl-1,3-dihydroisobenzofuran-5-yl)oxy]-3-pyridyl]-5,5-dimethyl-imidazolidine-2,4-dione (Example 51 of PCTGB2012/051278).

16. The method according to claim 1, wherein the compound of formula (I) is a prodrug and is functionalised at the secondary nitrogen of the hydantoin, as illustrated below:

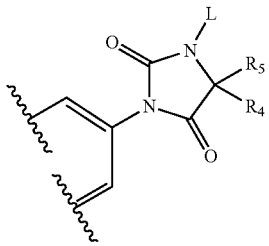

wherein L is selected from:
a) —PO(OH)⁻.M⁺, wherein M⁺ is a pharmaceutically acceptable monovalent counterion,
b) —PO(O⁻)$_2$.2M⁺,
c) —PO(O⁻)$_2$.D$^{2+}$, wherein D$^{2+}$ is a pharmaceutically acceptable divalent counterion,
d) —CH(R$^X$)—PO(OH)O⁻.M⁺, wherein Rx is hydrogen or C$_{1-3}$ alkyl,
e) —CH(R$^X$)—PO(O⁻)$_2$.2M⁺,
f) —CH(R$^X$)—PO(O⁻)$_2$.D$^{2+}$
g) —SO$_3$⁻.M⁺,
h) —CH(R$^X$)—SO$_3$⁻.M⁺, and
i) —CO—CH$_2$CH$_2$—CO$_2$.M⁺.

17. The method of claim 4 wherein the compound of formula (I) is administered up to 15 minutes in advance of an event which could cause noise-induced hearing loss.

18. The method of claim 7 wherein the compound of formula (I) is administered up to 15 minutes in advance of an event which could cause noise-induced hearing loss.

19. The method of claim 9 wherein the therapeutic agent is a steroidal anti-inflammatory agent.

20. The method of claim 19 wherein the anti-inflammatory agent is dexamethasone.

* * * * *